US011819663B2

(12) United States Patent
Marcoz et al.

(10) Patent No.: US 11,819,663 B2
(45) Date of Patent: Nov. 21, 2023

(54) AUTO-INJECTION DRUG DELIVERY DEVICE

(71) Applicant: BIOCORP PRODUCTION S.A., Issoire (FR)

(72) Inventors: Alain Marcoz, Montmorin (FR); Alexandre Pereira, Pérignat-lès-Sarliève (FR); Mathieu Pollard, Pont-du-Château (FR)

(73) Assignee: BIOCORP PRODUCTION S.A., Issoire (FR)

( * ) Notice: Subject to any disclaimer, the term of this patent is extended or adjusted under 35 U.S.C. 154(b) by 608 days.

(21) Appl. No.: 16/954,421

(22) PCT Filed: Dec. 19, 2017

(86) PCT No.: PCT/IB2017/001754
§ 371 (c)(1),
(2) Date: Jun. 16, 2020

(87) PCT Pub. No.: WO2019/122946
PCT Pub. Date: Jun. 27, 2019

(65) Prior Publication Data
US 2021/0077723 A1  Mar. 18, 2021

(51) Int. Cl.
*A61M 5/20* (2006.01)
*A61M 5/315* (2006.01)
*A61M 5/32* (2006.01)

(52) U.S. Cl.
CPC ........ *A61M 5/2033* (2013.01); *A61M 5/3157* (2013.01); *A61M 5/31568* (2013.01);
(Continued)

(58) Field of Classification Search
CPC ...... A61M 2005/3231; A61M 5/31596; A61M 5/19; A61M 5/31511; A61M 5/3286;
(Continued)

(56) References Cited

U.S. PATENT DOCUMENTS

2006/0153693 A1   7/2006 Fiechter et al.
2013/0245604 A1*  9/2013 Kouyoumjian ......... A61M 5/19
                                                    604/506
2016/0271326 A1*  9/2016 Slate ................... A61M 5/3134

FOREIGN PATENT DOCUMENTS

CN    104853788 A    6/2015
CN    107206186 A    8/2015
(Continued)

*Primary Examiner* — Amber R Stiles
*Assistant Examiner* — Nelson Louis Alvarado, Jr.
(74) *Attorney, Agent, or Firm* — Levine Bagade Han LLP

(57) ABSTRACT

The invention relates to an automatic injector device comprising a single-use, disposable, drug delivery assembly comprising a housing and a syringe assembly located at least partially within the housing, said syringe assembly including a plunger, a pre-filled unit-dose drug containing chamber, and needle, said plunger, drug containing chamber and needle being configured and dimensioned to function as an injection syringe; a reusable motorized transmission assembly comprising a housing, a motor and transmission assembly located within the housing, said transmission assembly being configured and dimensioned to engage the plunger of said syringe in the drug delivery assembly and expel said unit dose drug from the drug containing chamber, into the needle and out of the drug delivery assembly; said single-use disposable drug delivery assembly and said reusable motorized transmission assembly are in substantial axial alignment along a longitudinal axis defined by the syringe, plunger, pre-filled unit-dose drug containing chamber, and needle.

36 Claims, 10 Drawing Sheets

(52) U.S. Cl.
CPC ...... *A61M 5/31591* (2013.01); *A61M 5/3202* (2013.01); *A61M 2005/208* (2013.01); *A61M 2005/2013* (2013.01); *A61M 2005/3152* (2013.01); *A61M 2005/31588* (2013.01); *A61M 2205/273* (2013.01); *A61M 2205/3569* (2013.01)

(58) Field of Classification Search
CPC .. A61M 5/3295; A61M 5/329; A61M 5/3294; A61M 2005/2462; A61M 2005/287; A61M 2205/19; A61M 2205/276; A61M 5/2066; A61M 5/2448; A61M 5/284; A61J 1/201
See application file for complete search history.

(56) References Cited

FOREIGN PATENT DOCUMENTS

| | | |
|---|---|---|
| CN | 104703641 A | 9/2017 |
| WO | WO 2009/143255 A1 | 11/2009 |
| WO | WO 2014/008393 A1 | 1/2014 |
| WO | WO 2014/019997 A1 | 2/2014 |
| WO | WO 2014/037946 A1 | 3/2014 |

\* cited by examiner

AUTO-INJECTION DRUG DELIVERY DEVICE

CROSS-REFERENCE TO RELATED APPLICATIONS

This application is a U.S. national phase under 35 U.S.C. 371 of International Patent Application Number PCT/IB2017/001754 filed Dec. 19, 2017, the content of which is incorporated herein by reference in its entirety.

BACKGROUND OF THE INVENTION

The present invention relates generally to auto-injector devices and more particularly to such devices configured and functional to automatically, or semi-automatically, deliver a drug to a user. Typically in such devices, drug delivery occurs via a drug delivery assembly, generally comprising a syringe and hollow needle or cannula, with at least one drug containing chamber, and a drug flow path established between the drug containing chamber and the needle such that drug can be injected into the body of a user or patient or otherwise released from the drug delivery assembly. The syringe, also generally comprising a plunger, is activated to push the drug out of the drug containing chamber and into the needle, and from there either into the environment or, as is generally intended, into the body of a user or patient. Such devices as generally described above are well known in the art. In its simplest form, a hypodermic syringe is one such example.

In some drug delivery applications, there is a particular requirement to be able to control with precision an amount, or a dose, of drug to be delivered. As a result of this requirement, sophisticated dose setting systems have been developed and coupled to various drug delivery assemblies.

In other drug delivery applications, there is a requirement to allow only for a single use of the drug delivery assembly. The general aim of such a device is to prevent a recipient of the drug from either overusing the drug, or to facilitate adherence to a drug treatment regime by ensuring that any given drug delivery assembly cannot be re-used even after partial, failed, or incomplete delivery of a drug, for whatever reason.

In still yet other drug delivery applications, there is a requirement for ensuring that the drug dose contained in the drug delivery assembly is completely delivered. This is important for some drug treatment regimes, where, for example, pre-allotted unit doses provided to a recipient of the drug must be completely delivered or administered in order for the drug treatment regime to be considered successfully executed or observed.

The requirement for ensuring that the drug dose contained in the drug delivery assembly be completely delivered is particularly important for drugs for which viscosities may already normally be relatively high, for example, in the case of proteins, peptides, hormones, antibodies and the like. At high shear, as is often the case in syringe assemblies, the problem of ensuring complete injection of a unit dose of high viscosity drug can be compounded. For example, if a drug is injected through a small needle, e.g. a needle with a nominal outer diameter of 0.4128 mm, a nominal inner diameter of 0.210 mm and a nominal wall thickness of 0.1016 mm, over a total injection time of 10 seconds, the shear rate inside the needle is estimated to be approximately 160,000 $s^{-1}$. Varying requisite shear conditions and injection times, coupled with the specific viscosities of modern drug formulations, make designing a suitable drug delivery device a challenging and not necessarily obvious endeavor, especially for auto-injectors, as the configuration must, at the same time avoid, for example, damaging the drug containing chamber, which is usually made of glass, and yet still provide certainty that all of the unit dose of the drug has nonetheless been expelled from the chamber, along with a desire to be able to detect and/or represent to the user and/or act in response to user operation, certain functional states of the device, for example, dose setting, detection of skin contact, start of injection, end of injection, and the like.

An automatic injector is known from WO2014008393A1 which is adapted to receive a cartridge including a barrel, a needle, a plunger assembly, the auto-injector comprising a housing, a cartridge carrier for receiving a portion of the cartridge, a plunger carrier, at least one transfer instrument coupling the cartridge carrier to the plunger carrier, an elongated drive device enabling movement of the plunger carrier, the plunger carrier and/or the cartridge carrier including an opening for receiving the at least one transfer instrument, a motor and a transmission assembly coupling the motor to the elongated drive device. In the auto-injector device described in this document, the barrel, needle, plunger assembly and drug cartridge is insertable into, and removable from, a housing which completely encapsulates and enclosed the barrel, needle and plunger assembly. The housing is shown as being constituted of two parts, an upper part and a lower part, with a hinge along one side of the housing enabling the upper and lower parts to be movably attached with regard one to the other and thereby allow opening and closure of the housing. The housing is designed with a sufficiently hollowed out portion to allow for introduction, and removal when spent, of the cartridge, needle and plunger assembly. The removable battery powered motor drives a threaded screw which supports a movable carriage that meshes with and is indexed on the threads of the threaded screw and moves forward or backward in correspondence to activation of the motor to move in a forward or reverse direction. The Indexed movable carriage engages, upon activation of the motor to drive the threaded screw forwards, the plunger assembly to drive the plunger assembly forward and expel the drug contained in the drug cartridge from the cartridge into the needle and form there into the user of the auto-injector. This device is, to all intents and purposes, particularly complex and contains an excessive number of different moving and interacting parts which make mechanical reliability of the device a potential problem, not to mention economically unviable.

The devices currently known or described do not address or solve the problems and disadvantages exposed above, and there is consequently still an unmet need for a simplified automatic injector device, or auto-injector device for short, that overcomes these various limitations and problems.

SUMMARY

One object of the present invention is therefore an automatic injector device comprising:

a single-use, disposable, drug delivery assembly comprising a housing and a syringe assembly located at least partially within the housing, said syringe assembly including a plunger, a pre-filled unit-dose drug containing chamber, and needle, said plunger, drug containing chamber and needle being configured and dimensioned to function as an injection syringe;

a reusable motorized transmission assembly comprising a housing, a motor and transmission assembly located within the housing, said transmission assembly being configured and dimensioned to engage the plunger of said syringe in the drug delivery assembly and expel said unit dose drug from the drug containing chamber, into the needle and out of the drug delivery assembly;

wherein said single-use disposable drug delivery assembly and said reusable motorized transmission assembly are in substantial axial alignment along a longitudinal axis defined by the syringe, plunger, pre-filled unit-dose drug containing chamber, and needle; and wherein the housing of the single-use, disposable, drug delivery assembly is removably coupled to the housing of the reusable motorized transmission assembly via a coupling system configured and dimensioned to provide substantial axial alignment between said single-use disposable drug delivery assembly and said reusable motorized transmission assembly.

In one preferred embodiment, the coupling system is operable by hand. Alternatively, the coupling system might require the assistance of a machine, for coupling of the assemblies.

In one embodiment, the coupling system enables substantially axially aligned coupling of the single-use, disposable, drug delivery assembly and the reusable motorized transmission assembly together in that said coupling system comprises snap lock coupling members comprising a male, insertion part and a corresponding female, receiving part, disposed at one of a distal extremity of the housing of said reusable motorized transmission assembly and a proximal extremity of the housing of said single-use disposable drug delivery assembly or vice-versa. Preferably, said male insertion part is disposed at a proximal extremity of the housing of the single-use, drug delivery assembly, and said female receiving part is disposed at a distal extremity of the housing of the reusable motorized transmission assembly.

According to a further embodiment, the coupling system enables removal of the single-use, disposable, drug delivery assembly from the reusable motorized transmission assembly in that:

said coupling system comprises snap lock coupling members comprising a male, insertion part and a corresponding female, receiving part, disposed at one of a distal extremity of the housing of said reusable motorized transmission assembly and a proximal extremity of the housing of said single-use disposable drug delivery assembly or vice-versa; and said corresponding female, receiving part comprises a twist-release enabling member providing for twist-release of said male, insertion part from said female, receiving part.

In yet another embodiment, the drug delivery assembly further comprises a needle guard configured and dimensioned to be housed at least partially within the drug delivery assembly housing, and coaxially movable along the longitudinal axis between a first, shielding position completely covering a distal extremity of the needle, and a second, injection-ready position.

In a further embodiment, the drug delivery assembly further comprises a needle guard configured and dimensioned to be housed at least partially within the drug delivery assembly housing, and coaxially movable along the longitudinal axis between a first, shielding position completely covering a distal extremity of the needle, a second, injection-ready position, and a third, wake-up position.

According to still yet another embodiment, the drug delivery assembly further comprises a needle guard configured and dimensioned to be housed at least partially within the drug delivery assembly housing, and coaxially movable along the longitudinal axis between a first, shielding position completely covering a distal extremity of the needle, a second, injection-ready position, a third, wake-up position, and a fourth, irreversible, safety position located distally of said first position.

In a further embodiment, the drug delivery assembly further comprises a needle guard and a needle guard brake, wherein:

the needle guard is configured and dimensioned to be housed at least partially within the drug delivery assembly housing, and is coaxially movable along the longitudinal axis between at least a first, shielding position completely covering a distal extremity of the needle, and at least a second, injection position; and the needle guard brake is configured and dimensioned to selectively engage or disengage the needle guard to restrict and/or allow coaxial movement of said needle guard between the at least first, shielding position completely covering a distal extremity of the needle, and the at least second, injection-ready position.

According to another embodiment, the drug delivery assembly further comprises a needle guard brake, wherein said needle guard brake comprises:

a longitudinal body, housed at least partially within the drug delivery assembly body and having an own longitudinal axis disposed in spaced apart parallel alignment with the longitudinal axis of the syringe assembly, the longitudinal body having a proximal extremity and a distal extremity.

According to another embodiment, the needle guard brake further comprises drive motor gear engagement means located at the proximal extremity of the longitudinal body, configured and dimensioned to engage with, and be releasable from, a drive motor gear housed within the reusable motorized transmission assembly.

According to another embodiment, the drive motor gear engagement means located at the proximal extremity of the longitudinal body comprises a grooved bore located proximate, and extending up to, the proximal extremity of said longitudinal body.

According to yet another embodiment, the needle guard brake further comprises an abutment located at the distal extremity of the longitudinal body, said distal extremity abutment comprising a distal abutment surface and a proximal abutment surface, the distal abutment surface of the distal abutment being configured and dimensioned to engage:

before use of the device, in the first, shielding position, with a first inner wall surface of the drug delivery assembly housing.

According to yet another embodiment, the needle guard brake further comprises an abutment located at the distal extremity of the longitudinal body, said distal extremity abutment comprising a distal abutment surface and a proximal abutment surface, the proximal abutment surface of the distal abutment being configured and dimensioned to engage:

before use of the device, in the first, shielding position, with a distal surface of the peripheral flange of the needle guard.

According to yet another embodiment, the needle guard brake further comprises an intermediate abutment projection located on a peripheral surface of the longitudinal body between said distal and proximal extremities, which abutment projection engages with a proximal surface of the peripheral flange of the needle guard after said needle guard has moved passed the third, wake up position.

According to yet another embodiment, the needle guard brake is further defined in that the distal extremity abutment surfaces and the intermediate abutment projection are in substantial alignment on the longitudinal body.

According to yet another embodiment, the motor housed within said reusable motorized transmission assembly housing comprises a toothed drive motor gear configured and dimensioned to engage with the corresponding grooves of said drive motor gear engagement means located at the proximal extremity of the longitudinal body.

According to yet another embodiment, the needle guard brake further comprises a pre-constrained elastic disengagement assembly configured and dimensioned to:

disengage the drive motor gear engagement means of the longitudinal body from said drive motor gear; and bias said longitudinal body in a distal direction towards a second inner wall surface of the drug delivery assembly housing, where the second inner wall surface is different to and located in a distal direction from, the first inner wall surface.

According to yet another embodiment, the distal extremity abutment surface of the longitudinal abutment on the longitudinal body is configured and dimensioned to engage:

after disengagement of the needle brake, with the second inner wall surface of the drug delivery assembly housing, said second inner wall surface being different to, and located in a distal direction from, the first inner wall surface.

According to yet another embodiment, the pre-constrained elastic disengagement assembly comprises:

a coiled spring; and a retaining collar, the coiled spring being mounted around the longitudinal body and in biasing abutment against the retaining collar;

the retaining collar being formed around said longitudinal body and projecting radially therefrom;

the disengagement assembly being located on the longitudinal body at a fixed position between the proximal extremity and the abutment projection of the longitudinal body.

According to yet another embodiment, the drug delivery assembly housing further comprises an activation circuit configured to electrically wake up the automatic injector device when the needle guard is moved into the wake up position.

According to yet another embodiment, the activation circuit comprises a "wake-up" microswitch configured to send an activation or "wake-up" signal to a programmable control system located within (the reusable motorized transmission assembly, said activation signal being generated when the needle guard is moved into said third, or "wake-up" position over said switch.

According to yet another embodiment, the drug delivery assembly housing further comprises a skin sensor circuit, configured to determine whether a distal extremity of the needle guard is in contact with, or in close proximity to, the skin of a user.

According to yet another embodiment, the skin sensor circuit is connected to a capacitive resistance surface area located at the distal extremity of the needle guard.

According to yet another embodiment, the capacitive resistance surface area and the skin sensor circuit are connected electrically via a coiled spring located within the needle guard and coaxially mounted around the syringe assembly.

According to yet another embodiment, the activation circuit is connected to the programmable control system located within the reusable motorized transmission assembly via a severable electrical connection.

According to yet another embodiment, the single-use, disposable, drug delivery assembly further comprises a needle guard comprising switch activation means.

According to yet another embodiment, the switch activation means is a switch engagement ridge located longitudinally in axial longitudinal alignment with the longitudinal axis along the outer surface of said needle guard.

According to yet another embodiment, the switch activation means is a contiguous switch engagement ridge located along the outer surface of said needle guard.

According to yet another embodiment, the switch activation means is formed by a plurality of noncontiguous switch engagement ridges located in axial alignment along the outer surface of said needle guard.

According to yet another embodiment, the drug delivery assembly housing further comprises a second microswitch configured to send an "injection ready" signal to a programmable control system located within the reusable motorized transmission assembly, said "injection ready" signal being generated when the needle guard is moved into said second position over said switch, in which position the needle is fully exposed.

According to yet another embodiment, the second "injection ready" microswitch is in longitudinal axial alignment with said first "activation" microswitch.

According to yet another embodiment, the "injection ready" microswitch is activated by said switch activation means.

According to yet another embodiment, the transmission assembly further comprises:

a drive motor gear assembly;

a programmable control system configured to command and control the functioning of the automatic injector; and a screw threaded piston having a proximal extremity and a distal extremity, the screw threaded piston being connected to, and driven by, the drive motor assembly via a piston drive gear of the drive motor gear assembly the needle brake drive motor gear and the screw threaded piston drive gear being disposed within the drive motor gear assembly in a substantially parallel and spaced apart alignment, wherein the screw threaded piston drive gear is axially aligned with the longitudinal axis of the syringe assembly, and the needle brake drive motor gear is axially aligned with the longitudinal body;

the screw threaded piston engaging the plunger of the syringe via the distal extremity of said screw threaded piston in response to programmed motor driven movement of the drive motor gear assembly;

said programmed motor driven movement being commanded and controlled by the programmable control system.

According to yet another embodiment, the programmable control system is configured to effect any one of the operations comprising:

receiving a wake-up signal from the wake-up switch to wake the device and provide electrical power to the device;

receiving a signal from the skin sensor indicating that the needle guard is in proximity to, or in contact with, the skin of a user;

in response to receiving such a skin sensor signal, commanding and controlling the drive motor and drive motor gear assembly to cause the drive motor gear to rotate the longitudinal body about its longitudinal axis and thereby cause the distal abutment and the abutment projection to move out of abutment alignment, thereby disengaging the needle brake and allowing free proximal movement of the needle guard to the second, injection ready position;

upon receipt of a signal from the activation circuit that the needle guard has reached the second, injection position, command and control the drive motor and drive motor gear assembly to cause the screw threaded piston drive gear to rotate and drive the screw thread towards the plunger;

continue to drive the screw thread distally onto the plunger until it is determined that the injection cycle is completed.

According to yet another embodiment, the programmable control system is configured to determine completion of the injection cycle by electrical power consumption analysis of the drive motor.

BRIEF DESCRIPTION OF THE FIGURES

The invention will be further described in relation to the accompanying figures, provided for illustrative and non-limiting purposes of exemplary manifestations of the embodiments of the present invention, in which.

DETAILED DESCRIPTION

Figure 1:
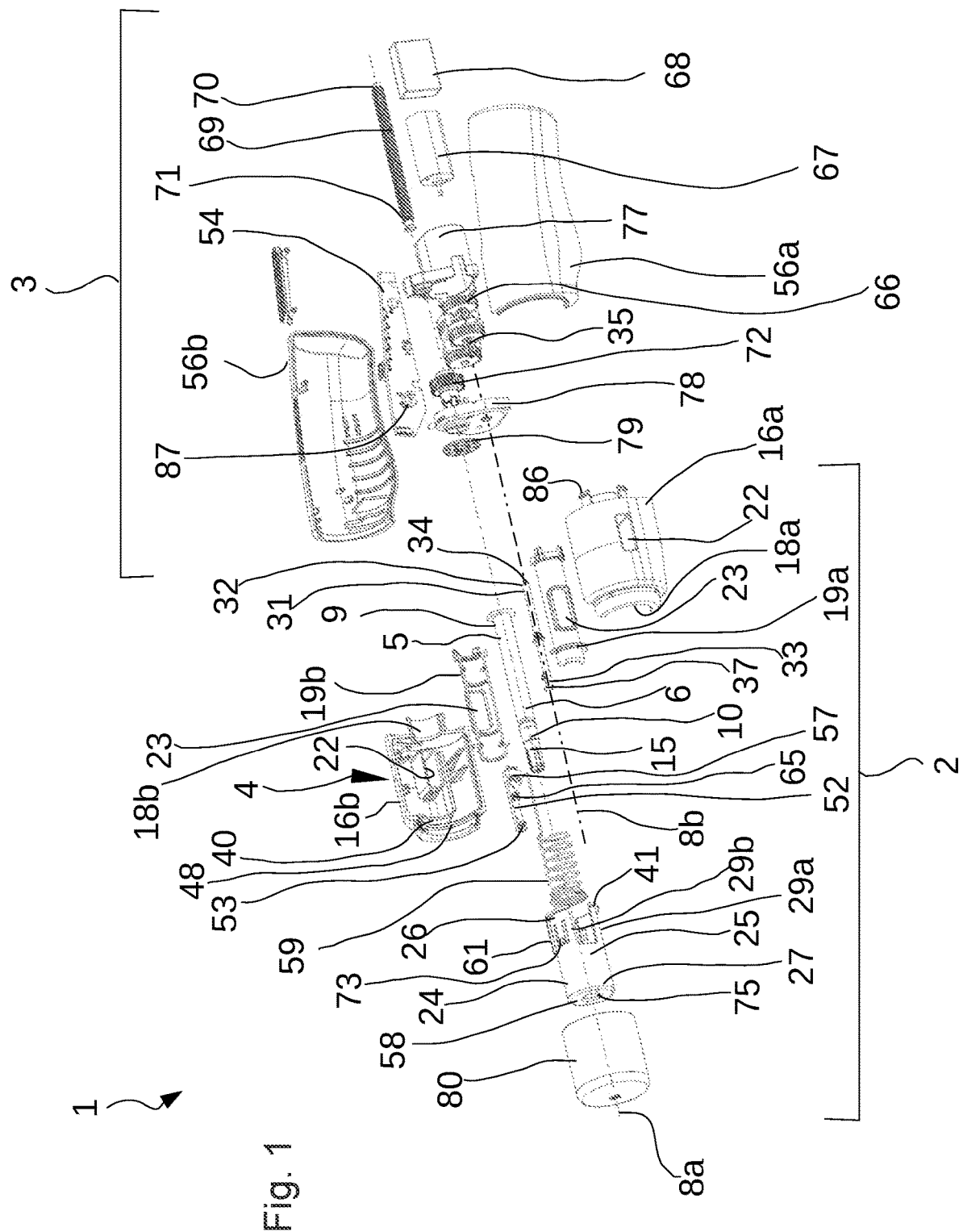
FIG. 1 is a schematic exploded perspective representation of an automatic injector device according to the invention.

Turning now to FIG. 1, a schematic perspective and exploded representation of an automatic injector device (1) according to the present invention is shown. The automatic injector device (1) in the exploded view of FIG. 1 comprises two main assemblies (2, 3), where the first assembly is a single-use, disposable, drug delivery assembly (2), and the second assembly is a reusable motorized transmission assembly (3). The single-use, disposable, drug delivery assembly (2) comprises a housing (4) and a syringe assembly (5) located at least partially within the housing (4), said syringe assembly (5) including a plunger (13), a pre-filled unit-dose drug containing chamber (14), and needle (11). The plunger (13), drug containing chamber and needle (11) are configured and dimensioned to function as an injection syringe, which in FIG. 1, is represented by a pre-filled, unit-dose syringe as known in the art. FIG. 1 does not show all of the details of the syringe assembly (5), however for the sake of completeness, and as mentioned above, the syringe assembly (S) Is shown in detail in FIG. 2 and subsequent figures and will be described hereafter in relation thereto. Accordingly, as can be seen from FIG. 2, the syringe assembly (5) comprises a generally longitudinal syringe body (6) having an inner longitudinal bore (7) therethrough, and defining a longitudinal axis (8a). The syringe body (6) further has a proximal extremity (9) and a distal extremity (10). The distal extremity (10) is closed by a cannula or needle (11) as is common in the art for injection syringes, mounted, for example, via a Luer mount, or directly, onto the distal extremity (10) of the syringe body (6), a proximal extremity (12) of the needle (11) or cannula being in fluid connection with the inner bore (7) of the syringe body (6) and thus the drug containing chamber (14). The syringe body (6) is further closed in a proximal direction by a plunger (13) located inside the bore (7) of the body (6). The initial position of the plunger (13) within the inner bore (7), together with the distal extremity (10) of said syringe body (6), define a drug containing chamber (14), the volume of which corresponds to a pre-allotted or predetermined unit dose volume of drug. Generally, in pre-filled unit-dose syringes, the plunger is only movable within the bore from an initial position to a final position in a distal direction, in other words, it is configured to move only in a direction that expels the drug contained in the drug containing chamber (14) out of the distal extremity (10) of the syringe body (6)

and into the needle (11). The needle (11), projecting out along the longitudinal axis (8) from the distal extremity (10) of the syringe body (6), is capped with a needle cap (15), which protects the needle before use, and prevents any accidental leakage of the drug from the syringe before use. The needle cap (15) is configured to be removable prior to injection to enable the needle to penetrate the skin of a user or the intended recipient of the drug and co-operates with, and is in contact with a device cap (80). Turning back to FIG. 1 once again, the drug delivery assembly (2) comprises a housing (4). The drug delivery assembly housing (4) substantially encases and surrounds the syringe assembly (5). In the illustration represented in FIG. 1, the drug delivery assembly housing (4) has a generally cylindrical body (16) of suitably molded or suitably machined material, such as a plastic material. In FIG. 1, and in one embodiment, the generally cylindrical body (16) of the drug delivery assembly housing (4) is represented by two mating body halves (16A, 16B). The two halves (16A, 16B), when assembled, form a longitudinal inner bore (17) that is configured to receive and hold, at least part of the syringe assembly (5). The inner walls (18A, 18B) of corresponding mating body halves (16A, 16B) are configured with suitable shapings, shoulders, ribs, grooves, projections and the like to locate and hold the syringe assembly (5) so that it doesn't move in any unwanted direction, and thereby also protecting the syringe from damage or tampering. The generally cylindrical body (16) with corresponding longitudinal bore can also be molded as a single piece into which the syringe assembly is then inserted via the longitudinal bore (17) of the body (16) and retained by suitable inner wall predefined shaping or elastic constraining elements. From the preceding description, it will be apparent that the generally cylindrical body (16) of the drag delivery assembly housing (4) is disposed coaxially around the syringe assembly. Alternatively to direct locating and holding of the syringe assembly (5) by the cylindrical body (16) described above, and as further illustrated in FIG. 1, the single-use, disposable, drug delivery assembly (2) further comprises a syringe assembly holder (19). As with the generally cylindrical body (16), such a syringe assembly holder (19) can also be made of a suitable plastic material and directly molded as a single piece comprising a generally longitudinal body (20) and having a longitudinal bore, into which the syringe assembly is inserted and retained, or as illustrated in FIG. 1, comprise two halves (19A, 19B). The two halves (19A, 19B) of the syringe assembly holder, when assembled, thus form a longitudinal inner bore (21), and the inner walls of each half (19A, 19B) are configured to receive and hold, for example via projecting semi-circular ribs located along the length of the body (20), and directly bear upon ah external surface of the syringe body (6) of the syringe assembly (5). In a similar manner, the outer walls of said syringe assembly holder body (20) are configured to mate with and be held and seated by corresponding projections, walls, ribs, grooves and the like provided on the inner walls (18A, 18B) of the generally cylindrical body (16) of the housing (4). As can further be seen from FIG. 1, both the generally cylindrical body (16) of the drug delivery assembly housing (4) and the syringe assembly holder (19) comprise aligned openings (22, 23) provided on at least one side of the respective bodies (16, 19). These openings (22, 23) allow for a line of sight from the outside of the automatic injector device to the outer wall of the syringe body (6). The openings (22, 23) are generally aligned with the drug containing chamber and are configured and dimensioned to function in coordination with a transparent or translucent wall of the syringe body to enable a user of the automatic injector device to visually check that the drug contained within the drug containing chamber has been expelled, or else observe-that an error has occurred where drug might have been left after a partial injection movement in the drug containing chamber (14), and thus that the unit-dose not completely administered.

The single-use, disposable, drug delivery assembly (2) further comprises a needle guard (24) configured and dimensioned to be housed at least partially within the drug delivery assembly housing (4), and coaxially movable along the longitudinal axis (8) between a first, shielding position completely covering a distal extremity of the needle, and a second, injection-ready position exposing the distal extremity of the needle (11). As exemplified in FIG. 1, the needle guard (24) is represented by a substantially cylindrical body (25) having a proximal extremity (26) and a distal extremity (27). The needle guard (24) is configured and shaped to surround at least partly the syringe assembly (6) and syringe assembly holder (19), and move slidingly in a proximal and distal direction and coaxially in relation thereto. In addition, the needle guard (24) is held in sliding coaxial location relative to the syringe assembly and syringe assembly holder (19) by the generally cylindrical body (16) of the drug delivery assembly housing (4). In other words, the needle guard is sandwiched between the inner walls of the cylindrical body (16) and the outer walls of the syringe assembly holder (19). It should be noted that the sliding movements of the needle guard (24) both in a proximal and a distal direction, and the relative positions that the needle guard (24) can adopt along the longitudinal axis (8), are controlled by interaction of the needle guard (24) with the inner wall projections (40, 48) of the generally cylindrical body (16) and further means as will be described hereinafter. As has been mentioned above, the needle guard (24) is configured and dimensioned to be slidingly movable between a first, shielding position completely covering a distal extremity of the needle, and a second, injection-ready position allowing for injection of the drug in the drug containing chamber to proceed. The drug delivery assembly (2) is farther configured such that the needle guard (24) can adopt two further positions of note: a third, wake-up position located between said first and second positions, and a fourth, irreversible, safety position located distally of the first position and from which the needle guard can no longer be moved either in a proximal or a distal direction. In the fourth, safety position, the only possibility with regard to manipulating the device is to detach and remove the single use drug delivery assembly to be thrown away, hence the use of the expressions "single-use" and "disposable" when referring to this assembly. The various positions of the needle guard will be discussed further hereinafter in relation to the other figures.

As mentioned above, the needle guard (24) has a substantially cylindrical body (25) with a proximal extremity (26) and a distal extremity (27). In the embodiment shown in FIG. 1, the substantially cylindrical body (25) of the needle guard (24) extends from the distal extremity (27), towards the proximal extremity (26), the walls (28) of the body (25) becoming non-contiguous around a periphery of the body in the direction of the proximal extremity (26) thereby forming a pair of proximal legs (29A, 29B) extending from pan of the way along the length of the body (25) towards the proximal extremity (26). The proximal extremity (26) of the body (25) is provided with a peripheral flange (41) having a proximal surface (42), a distal surface (43), and a peripheral edge (44) joining said proximal (42) and distal (43) surfaces to form the flange (41). The proximal (42) and distal (43) surfaces of the peripheral flange (41)

interact with other means comprised in the drug delivery assembly as will be described hereinafter. The distal extremity (27) of the body (25) is provided with a needle exit opening (75) to allow the needle (11) to move through the opening of the distal extremity (27) as the needle guard (24) moves slidingly in a proximal direction. The needle exit opening is furthermore configured and dimensioned to be wide enough to allow the needle cap (15) to pass unhindered through said opening (75) when the needle cap (15) is withdrawn. The needle cap (15) is configured to be connected, for example, by longitudinal grooves (74) or other similar recesses provided in the surface of the needle cap (15) to elastic grip means (76) on a device cap (80). The elastic grip means (76) of the device cap (80) are configured to project from an inner surface of a distal extremity of the device cap (80) through the needle exit opening (75) and enter into elastic friction grip with the grooves or recesses (74) on the surface of the needle cap (15), for example, by push fit or click fit elastic grip. When the device cap (80) is removed, the elastic grip exerted by the elastic grip means (76) also pulls on the needle cap (15) thereby removing the same at the same time as the device cap (80) and exposing the needle within the needle guard (24).

The drug delivery assembly (2) further comprises a needle guard brake (30). The needle guard brake (30) is configured and dimensioned to selectively engage or disengage the needle guard (24) to restrict and/or allow coaxial movement of said needle guard (24) between the at least first, shielding position completely covering a distal extremity of the needle (11), and the at least second, injection-ready position. The needle guard brake (30) interacts with the needle guard (24) to prevent, or allow, the latter to move slidingly and co-axially along the longitudinal axis within the housing (4) to at least some of the first, second, third and fourth positions indicated above. In particular, the needle guard brake (30) is responsible for some of the safety features built into the automatic injector device since, and by preventing unwanted sliding movement of the needle guard, it ensures that any undesired or unsuitable attempt to inject drug from the drug containing chamber via the needle before the device is in the correct position to be used, is prevented, for example in the case when the device is insufficiently closely positioned in proximity to the skin. The needle guard brake (30) comprises a longitudinal body (31), housed at least partially within the drug delivery assembly housing (4) and having an own longitudinal axis (8b) disposed in spaced apart parallel alignment with the longitudinal axis (8a) of the syringe assembly, the longitudinal body (31) having a proximal extremity (32) and a distal extremity (33). The needle guard brake (30) further comprises drive motor gear engagement means (34) located at the proximal extremity (32) of the longitudinal body (31), configured and dimensioned to engage with, and be releasable from, a drive motor gear (35) housed within the reusable motorized transmission assembly (3). As can be seen from FIG. 1, the needle guard brake is generally rod-shaped, and can be made from any suitably rigid material, for example a molded plastic, or a metal such as a metal alloy, although a shock and stress resistant plastic is the preferred material. The drive motor gear engagement means (34) located at the proximal extremity (32) of the longitudinal body (31) comprises a projection forming an integral part of the longitudinal body, bearing a grooved surface located proximate, and extending up to, the proximal extremity (32) of said longitudinal body. The grooved surface of the drive motor engagement means (34) has grooves (36) which are oriented along and coaxially with the longitudinal axis of the longitudinal body (31) and correspond to, and cooperate with, a toothed cog (84) provided on, or mounted in axial alignment with, the drive motor gear (35). The needle guard brake (30) further comprises an abutment (37) located at the distal extremity (33) of the longitudinal body (31), said distal extremity abutment (37) comprising a distal abutment surface (39) and a proximal abutment surface (38), the distal abutment surface (39) of the distal abutment (37) being configured and dimensioned to engage, before use of the device, in the first, shielding position, with a first inner wall surface (40) of the drug delivery assembly housing (4). In such a position, the needle guard brake (30) abuts the first inner wall surface (40) via the distal abutment surface (39) of the distal abutment (37) and the needle brake (30) cannot be disengaged without damaging the longitudinal body. The proximal abutment surface (38) of the distal abutment (37) is configured and dimensioned to engage before use of the device, in the first, shielding position, with the distal surface (43) of the peripheral flange (41) of the needle guard. The distal abutment (37) projects radially outwards from the distal extremity (33) of the needle guard brake (30), and is configured and dimensioned to form a substantially crescent-shaped or arcuate outer curved edge (45), with walls extending from the longitudinal body (31) to the edge (45) to form the respective proximal (38) and distal (39) abutment surfaces. As a result of the crescent-shaped or arcuate outer curved edge, the abutment surfaces (38, 39) do not completely engage with corresponding abutting surfaces, such as the inner wall projections (40, 48) of the housing (4) or the proximal (42) and distal (43) surfaces of the peripheral flange (41), said surface engagement between the respective abutment surfaces (38, 39) and the inner wall projections (40, 48) being dependent on the rotation position of the longitudinal body (31). This also allows for the inner wall surfaces (40, 48) of the housing (4) to be formed as arcuate or substantially arcuate projecting surfaces, for example, which project from an inner wall of the housing (4) into an inner space, or bore, created by the walls of the housing. As the distal abutment (37) is rotated about the longitudinal axis of the longitudinal body through motion communicated via the drive motor gear engagement means (34) located at the proximal extremity (32) of the longitudinal body (31), the proximal (38) and distal (39) abutting surfaces are moved around the body to the same extent, but their substantially crescent-shaped, or arcuate surfaces, move away from or towards a corresponding abutment surface of the inner wall of the housing (4) or the distal (43) or proximal (42) surfaces of the peripheral flange (41). The angle of rotation generally configured for the longitudinal body (31) about its longitudinal axis (8b) is between 0° and 180°, in other words, a half-circle rotation, where 0° preferably corresponds to a position in which the distal abutting surface (39) of the distal abutment (37) is in full surface abutment with the first inner wall projecting surface (40). In this way, it is possible to selectively control the needle guard brake so that it blocks sliding movement of the needle guard (24) by abutment of the peripheral flange (41) against either the corresponding proximal (38) and/or distal (39) abutment surfaces of the distal abutment (37). Additionally, the needle guard brake (30) further comprises an intermediate abutment projection (46) located on a peripheral surface of the longitudinal body, and extending radially therefrom, located between said distal (33) and proximal (32) extremities, which abutment projection engages with a proximal surface (42) of the peripheral flange (41) of the needle guard (24), after said needle guard has moved passed the third, wake up position. As is apparent from the figures, the needle guard brake (30) is further defined in that the distal abutment (37) proximal (38) and distal (39) surfaces, and the intermediate abutment projection (46) are in substantial alignment on, and spaced apart along, the peripheral surface of the longitudinal body (31). The distance between the distal abutment (37) and the abutment projection (46) is configured and determined in advance when manufacturing and assembling the device to allow the needle guard to move slidingly and coaxially along the longitudinal axis of the syringe assembly from the first, needle shielded position, in which the distal surface (42) of the peripheral flange (41) abuts the proximal surface (38) of the distal abutment (37), in the direction of the second, injection-ready position, whilst at the same time, and only if no skin contact or sufficient proximity with said skin has been detected by a skin sensor circuit (57), preventing further sliding movement of the needle guard (24) towards said second, injection-ready position. In such an event, i.e. where no skin has been detected by the skin circuit, the needle guard brake (30) will not have been disengaged, abutment of the proximal surface (42) of the peripheral flange (41) of the needle guard against the abutment projection (46) of the needle guard brake (30) will occur.

Disengagement of the cylindrical body (31) from its abutting positions will be described as follows. Upon detection by the skin sensor circuit (57) of suitable proximity to the skin of the distal extremity of the needle guard, a corresponding signal is sent to, and received by a programmable control system (54). The programmable control system (54) then commands a motor (67) and drive motor gear assembly (66) to cause rotation of the drive motor gear (35). Suitable rotation, say, up to 180° of rotation about the longitudinal axis (8b), depending on the surface area configuration of the distal abutment (37) and the abutment projection (46), of the longitudinal body (31), and operated via the drive motor gear (35) through the drive motor gear engagement means (34), causes corresponding rotation of the aligned distal abutment (37) and abutment projection (46), which moves the distal abutment (37) into a position away from, and out of abutting contact with, the first inner wall projecting surface (40). The needle guard brake (30) further comprises a pre-constrained elastic disengagement assembly (47) configured and dimensioned to disengage the drive motor gear engagement means (34) of the longitudinal body (31) from the drive motor gear (35) and bias the longitudinal body (31) in a distal direction towards a second inner wall projection surface (48) of the drug delivery assembly housing, where the second inner wall projection surface (48) is different to and located in a distal direction from, the first inner wall projection surface (40). In this manner, the disengagement means releases the needle guard brake, and the needle guard is therefore free to continue its sliding movement in a proximal direction towards the second, injection-ready, position. In one preferred embodiment, as illustrated in the figures, the pre-constrained elastic disengagement assembly (47) comprises a coiled spring (49) and a retaining collar (50), the coiled spring (49) being mounted around the longitudinal body (31) and in biasing abutment against the retaining collar (50), the retaining collar (50) being formed around said longitudinal body (31) and projecting radially therefrom. The disengagement assembly (47) is thus located on the longitudinal body (31) at a fixed position between the proximal extremity and the abutment projection (46) of the longitudinal body. When the needle brake is in the unreleased position, the proximal end (32) engages the motor drive gear (35) via the drive motor gear engagement means (34). Additionally, the coiled spring (49) is compressed against the retaining collar (50), and acts as a store of kinetic energy. As has been mentioned above, when the longitudinal body (31) is rotated about the body's longitudinal axis by the cooperative rotational movement imparted by the drive motor gear (35) and drive motor gear engagement means (34) to move the distal abutment surface of the distal abutment (37) from abutment against the first inner wall projection surface (40) into free space, the elastic pre-constraint and pent-up kinetic energy caused by the spring against the collar is released. The release of energy is directed towards the retaining collar (50) which, being fixed to the longitudinal body (31), drives said longitudinal body in a distal direction so that the distal abutment (37) comes to rest in abutment against the second inner wall projection surface (48). At the same time, the drive motor gear engagement means (34) located at the proximal extremity of the longitudinal body is also disengaged from the drive motor gear (35). In this way, the needle guard brake (30) is located in a completely disengaged position.

The drug delivery assembly also further comprises an activation circuit (51) configured to electrically wake up the automatic injector device (1) when the needle guard (24) is moved into the wake up position. The expression "electrically wake-up" refers to the situation in which the automatic injector device contains electric and electronic components, but remains dormant for as long as it is not woken up, in other words, the device is either completely switched off, or in a power saving mode, and most of the electronic circuitry included in the device is either asleep or completely inactive. The automatic injector device is thus provided with the means to be woken up and activate the various circuitry and electronic components. The activation circuit (51), which can be mounted at least partly on a printed circuit board (52) housed within the housing (4) of the drug delivery assembly, further comprises a "wake-up" microswitch (53) configured to send an activation or "wake-up" signal to a programmable control system (54) located within the reusable motorized transmission assembly (3), said activation or "wake-up" signal being generated when the needle guard (24) is moved into said third, or "wake-up" position over said switch (53). The wake up microswitch (53) is thus connected to the printed circuit board (52) housed within the housing (4). The activation circuit (51) can be connected to the programmable control system (54) by a severable electrical connection (55), such as an array of sprung-loaded electrical connectors (55A, 55B) mounted respectively in the drag delivery assembly housing and motorized transmission assembly housing (56A, 56B). Such connectors are known in the art. In this way, an electrical connection can be maintained when the drug-delivery assembly and motorized transmission assembly are connected to each other during use of the device, and severed again when the single-use drug-delivery delivery assembly has served its useful purpose.

As has been mentioned briefly above, the drug delivery assembly housing (4) further comprises a skin sensor circuit (57), configured to determine whether a distal extremity (27) of the needle guard (24) is in contact with, or in close proximity to, the skin of a user. The skin sensor circuit (57) is connected to a capacitive resistance surface area (58) located at, or adjacent, the distal extremity (27) of the needle guard. Such capacitive resistance surfaces are known in the art, for example as used in smartphones and tablets with touchscreen interfaces. The main principle of such capacitive resistance surfaces is that when the skin of a user is brought near to, or to bear upon, such a surface, even indirectly, for example, when the capacitive resistance surface lies underneath a layer of another material, it causes a change in the electrical resistance of the circuit generated between the skin which is grounded or earthed, and the object that it is either touching or with which it is in close contact. Such a change in electrical resistance can be measured by an appropriately configured skin sensor circuit (57). The skin sensor circuit can helpfully be located on the same printed circuit board (52) as the activation circuit (51). The skin sensor circuit (57) is therefore also connected to the programmable control system (54). The skin sensor circuit (57) functions to determine whether or not the user has brought the device sufficiently closely to the skin in order for an injection to be carried out safely and in accordance with standard injection operating procedures. In the event of detection of a signal indicating that the skin is sufficiently close to the distal extremity of the automatic injector device, the skin sensor circuit (57) sends a corresponding signal to the programmable control system (54). The capacitive resistance surface area (58) and the skin sensor circuit (57) are connected electrically, for example and advantageously via a coiled spring (59) located within the needle guard (24) and coaxially mounted around the syringe assembly, although said electrical connection could alternatively be established by equivalent means. The coiled spring (59) bears partly upon an inner wall (60) of the distal extremity (27) of the needle guard, and in the first, second and third positions, the coiled spring is in a constrained configuration, storing kinetic energy. After disengagement of the needle guard brake (30), and subsequent injection of the drug, the coiled spring (59) is free to release its pent up kinetic energy and moves from the constrained configuration, along and co-axially around the longitudinal axis (8) inside the needle guard, in the distal direction to an unconstrained configuration, in which the spring (59) is substantially relaxed. Since the coiled spring (59) abuts the inner wall (60) of the distal extremity (27) of the needle guard, the latter is pushed in a distal direction so that the needle guard body (25) comes Into abutment with a distal extremity portion of the housing (4), and the needle guard body (25) is held in abutment against a narrowed diameter projecting inner wall of the housing (4) by projecting hooks (73) provided on an outside surface wall of the needle guard body (25), which projecting hooks (73) elastically and frictionally engage with said narrowed diameter projecting inner wall of the housing (4) of the drug delivery assembly (2), preventing the needle guard body (25) from being moved subsequently in a proximal direction to reveal the needle again. In this way, the needle guard (24) has entered the fourth, irreversible position, which position is considered to be the final safety position, as the drug delivery assembly (2) of the automatic injector device can no longer be used. Note that the needle guard can further be configured so that the edge (44) of the peripheral flange (41) abuts against a cut away section of an inner wall projection (40) of the housing (4), preventing any wiggle or lateral movement of the needle guard body (25) out of alignment with the longitudinal axis (8*a*) in any manual attempt to force it to move in a distal or proximal direction.

Although not mentioned thus far, the needle guard (24) can further comprise switch activation means. The switch activation means could actually be represented by the peripheral flange (41), as this moves along the longitudinal axis (8*a*) of the syringe assembly and could be positioned to cross the pathway of the activation switch. However, in a preferred and advantageous embodiment, the switch activation means is a switch engagement ridge (61) located longitudinally in spaced apart axial alignment with the longitudinal axis (8*a*) along the outer surface of said needle guard body (25). The activation switch means can advantageously be a contiguous switch engagement ridge (61) located along the outer surface of said needle guard body (25), or formed alternatively by a plurality of non-contiguous switch engagement ridges located in axial alignment along the outer surface of said needle guard body (25). The switch engagement ridge, having a proximal extremity (62) and a distal extremity (63), and being mounted on the outer surface of said needle guard body (25), moves along the longitudinal axis with, and in a similar manner to, the needle guard body (25), and is provided with a suitably configured and inclined, or angled, ridge surface (64). The switch engagement ridge can be likened to an "A-frame" shaped body having a substantially triangular cross-section with an apex projecting radially outwards from the needle guard body (25) outer surface. In this way, the angled surfaces either side of the apex of the "A" form at least one angled ridge surface (64). The angled ridge surface (64) comes into contact with the microswitch (53) which is pressed down by contact of the microswitch (53) with the angled surface (64) as the switch engagement ridge (61) moves in a proximal direction. In this way the microswitch is activated.

The drug delivery assembly housing further comprises a second microswitch (65) configured to send an "injection ready" signal to the programmable control system (54) located within the reusable motorized transmission assembly (4). The "injection ready" signal is generated when the needle guard (24), and therefore corresponding switch activation means which, as illustrated in the figures is the switch activation ridge (61), are moved in a proximal direction into said second position, with the angled ridge surface (64) contacting the second microswitch. When the needle guard (24) reaches this second position, the injector needle is fully exposed. In such a configuration, the second "injection ready" microswitch (65) is optimally and advantageously in longitudinal axial alignment with the first "activation" microswitch (53). In a particularly advantageous embodiment as exemplified in the figures, the "injection ready" is only sent to the programmable control system (54) when both switches are simultaneously activated, i.e. when the angled ridge surface (64) of the switch activation ridge (61) is in simultaneous contact with both the activation switch (53) and injection ready switch (65).

As illustrated in FIGS. 1, the transmission assembly comprises a drive motor gear assembly (66), a drive motor (67), a power supply (68) for supplying power to the device, for example, a rechargeable or simple battery, a programmable control system (54) configured to command and control the functioning of the automatic injector device, and a screw threaded piston (69) having a proximal extremity (70) and a distal extremity (71). The screw threaded piston (69) is connected to the drive motor gear assembly (66), which is suitably housed in a gear assembly housing (77, 78). The screw threaded piston (69) is driven by a piston drive gear (72) of the drive motor gear assembly (66). The needle brake drive motor gear (35) and the screw threaded piston drive gear (72) are disposed within the drive motor gear assembly (66) in a substantially parallel and spaced apart alignment, wherein the screw threaded piston drive gear (72) is axially aligned with the longitudinal axis of the syringe assembly, and the needle brake drive motor gear (35) is axially aligned with the longitudinal body (31). The screw threaded piston (69) engages the plunger of the syringe via the distal extremity (71) of said screw threaded piston (72) in response to programmed motor driven movement of the drive motor gear assembly (66). The programmed motor driven movement is commanded and controlled by the programmable control system (54), which is responsible for sending, and receiving, various command signals within the device, and processing said signals to effect either disengagement of the needle guard brake (30), or activation of the screw threaded piston (69) so that the latter may push the plunger (13) and expel the drug from the drug containing chamber. The transmission assembly further comprises a coding wheel (79) which is indexed to the rotational movement of the piston drive gear (72) and bears a series of markings and/or indentations located on at least one circumferential surface of said wheel (79), and disposed around the circumference of the wheel (79). As the threaded piston (69) is moved forward in the proximal direction by the motor to push drug out of the drug containing chamber, an optical reader head (87), connected to the programmable control system and located in a position over at least part of one of the circumferential surfaces of the wheel (79), reads the indentations and/or markings. Each marking and or indentation corresponds to a set number of rotations of the threaded piston (69) and/or the distance travelled by said piston. These readings are converted to signals and sent to the programmable control system (54) for processing. The signals received by the programmable control system (54) from the optical reader head (87) are used by the programmable control system (54) to determine when the piston (69) has nearly reached the end of its permitted and preconfigured distance of travel. When this event occurs, the programmable control system (54) commands the power supply (68), and/or the motor (67), to reduce its power output, thereby slowing down said motor just before the end of the injection step is reached. In this way, potential damage to the drug delivery assembly, and/or the transmission assembly components, is reduced and/or avoided.

Figure 2:
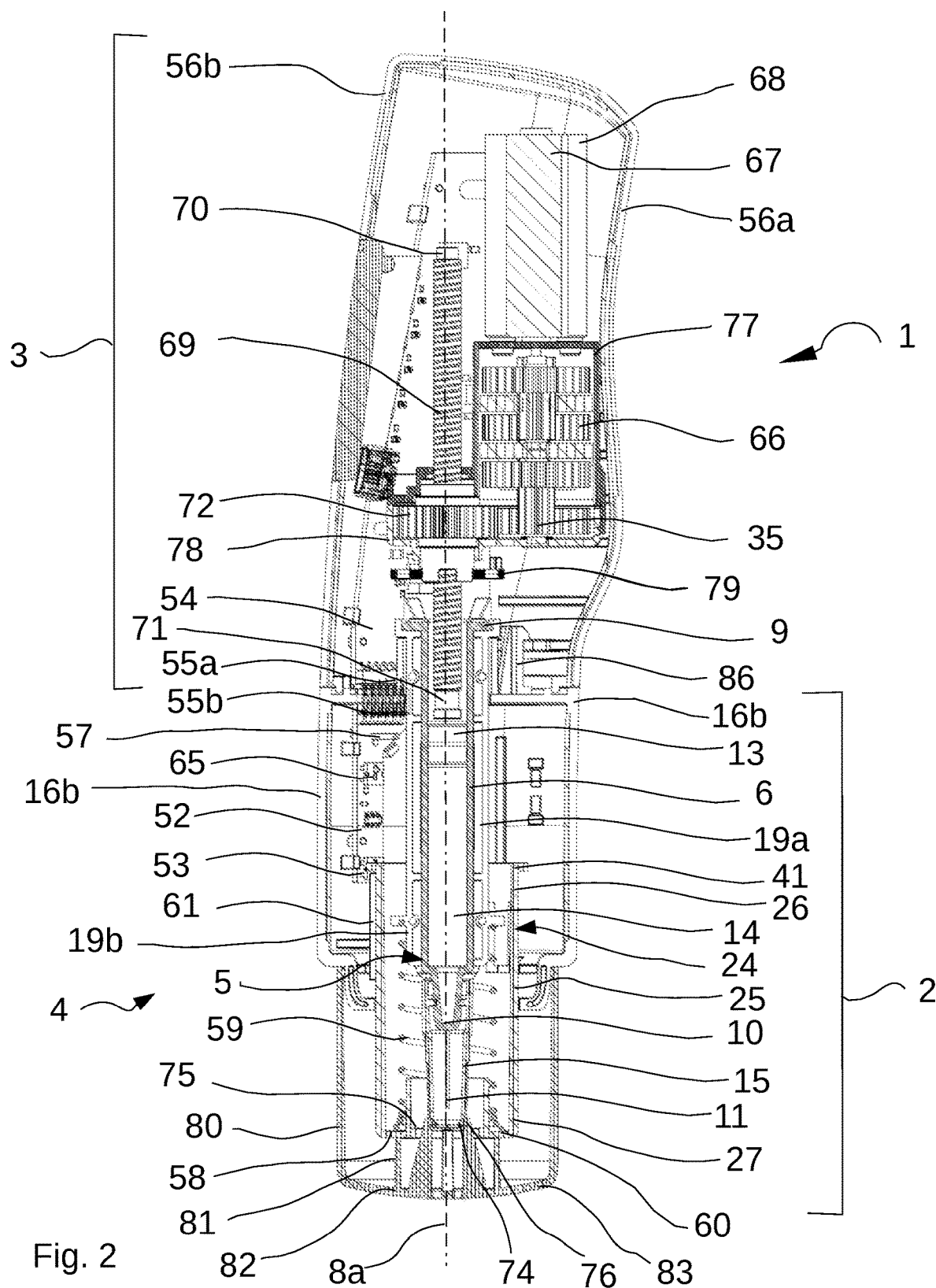
FIG. 2 is a schematic cross-sectional representation of an automatic injector device according to the invention.

The transmission assembly housing (56a, 56b) is physically coupled to the drug delivery assembly housing (4, 16a, 16b) via respective and corresponding female male interlocking, or snap-fit, snap-lock parts. The male insertion parts (86) can be seen in FIG. 2, in which they are located at a proximal extremity of the drug delivery assembly housing, and are inserted into a corresponding and respective female receiving parts, for example a cut-away portion in a projecting wall of the transmission assembly housing, adapted to receive the male insertion part (86) in elastic friction engagement. In FIG. 2, the male insertion parts are hooked elastic members (86), which can be snap-fitted into the female receiving parts, which are the cut-away areas as indicated above. The two housings can be separated one from the other by pushing one housing slightly towards the other and twisting, e.g. the drug-delivery housing (4), in an anti-clockwise direction. This forces the elastic hook of the male insertion part to move against a slightly raised and angled section of material provided in the female receiving part to the point where the elastic hook overcomes the resistance caused by the raised and angled section, whereby the hook, under continued anticlockwise rotation, enters a further cut-away section of projecting wall of the transmission assembly housing which is configured to allow withdrawal of the elastic hook, along the longitudinal axis (8a) and thereby separation of the drug delivery assembly housing (4) from the transmission assembly housing.

In addition, the programmable control system is configured to effect any one of the operations comprising:

receiving a wake-up signal from the wake-up switch (53) to wake the automatic injector device and provide electrical power to the remainder of the device circuits;

receiving a signal from the skin sensor (57) indicating that the needle guard is in proximity to, or in contact with, the skin of a user;

in response to receiving such a skin sensor signal, commanding and controlling the drive motor (67) and drive motor gear assembly (66) to cause the drive motor gear to rotate the longitudinal body (31) about its longitudinal axis and thereby cause the distal abutment and the abutment projection to move out of abutment alignment, thereby disengaging the needle brake and allowing free proximal movement of the needle guard to the second, injection ready position;

upon receipt of a signal from the activation circuit that the needle guard has reached the second, injection position, command and control the drive motor and drive motor gear assembly to cause the screw threaded piston drive gear to rotate and drive the screw thread towards the plunger;

continue to drive the screw thread distally onto the plunger until it is determined that the injection cycle is completed.

Additionally, and advantageously, the programmable control system is further configured to determine completion of the injection cycle by electrical power consumption analysis of the drive motor. For example, when the plunger reaches the distal extremity of the drug containing chamber, the screw threaded piston encounters resistance that increases as it attempts to push the piston further in the distal direction against the distal extremity of the drug containing chamber of the syringe. This physical resistance translates to an increased power consumption by the motor, which is detected by the programmable control system. The programmable control system can for example be suitably configured to store a limit of electrical power consumption above which the programmable control system determines that all of the drug has been expelled and that the injection step has been completed.

There now follows a further description of the functioning of the device with particular reference to FIGS. 2 to 20, in which like elements or components of the device are referenced, where appropriate, identically to those in FIG. 1.

Turning now to FIG. 2, a schematic cross-sectional representation of an automatic injector device according to the invention is presented. This representation differs mainly from that of FIG. 1 in that the needle brake is not illustrated for the sake of simplicity. However, in complement to FIG. 1, the syringe assembly (5) is illustrated, and shows the presence of the syringe body (6), the plunger (13), drug containing chamber (14) and needle (11). The representation of FIG. 2 shows the automatic injector device in an initial state, in which the device cap (80) is still on the device (1). As can be seen from FIG. 2, when the device cap (80) is still on the device, said cap maintains the needle guard in a fixed initial position, also known as the zero position. In FIG. 2, this is achieved by projections (81) of the material constituting the cap extending from an inner, or inside surface (82) of the cap at its distal extremity (83), in a proximal direction, the proximal extremities of said projections (81) pushing down on the distal extremity of the needle guard body (25). The device (80) further comprises elastic grip means located at its proximal extremity which engage in elastic friction grip with a suitably shaped shoulder of the housing (4) of the drug delivery assembly. The needle guard (24) is thus located in a zero position or initial position, in which the peripheral flange (41) is located proximally of inner projection wall (40) and therefore does not abut the proximal (38) surface of the distal abutment (37) of the needle brake (30).

Figure 3:
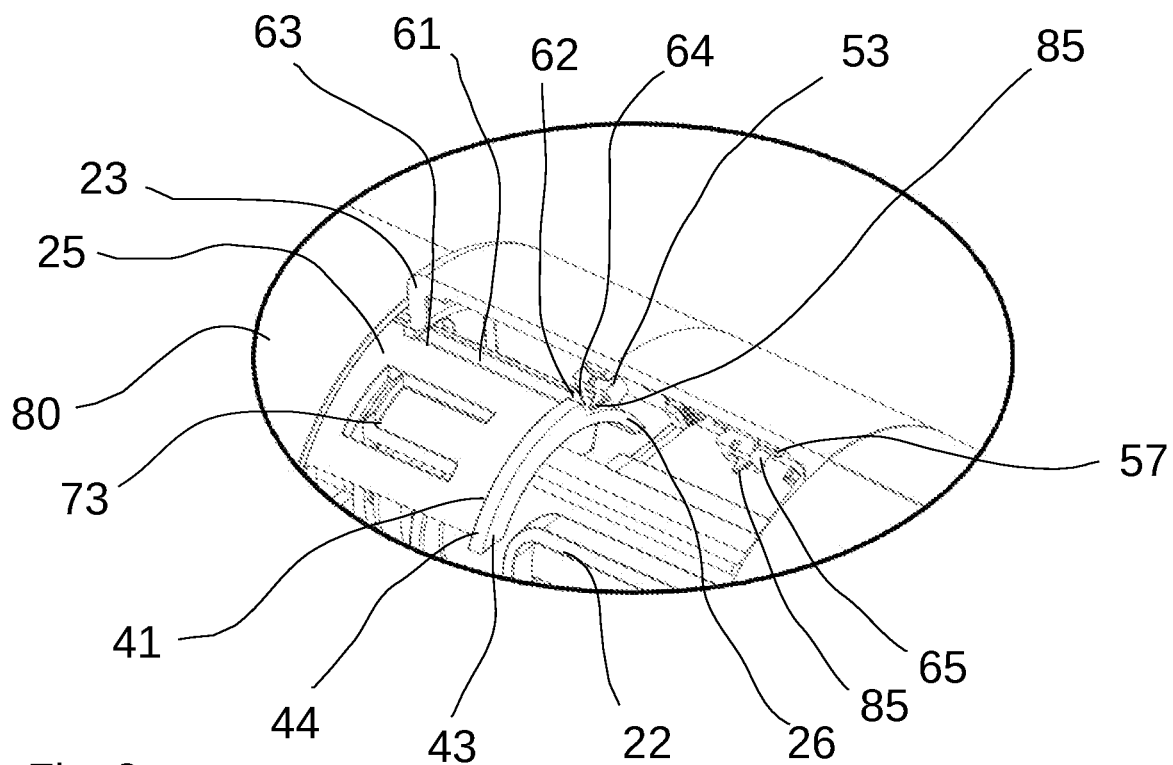
FIG. 3 is a schematic magnified torn away perspective representation showing a detail of a needle guard comprised in the single-use, disposable, drug delivery assembly of the device shown in FIG. 2.

Additionally, as illustrated in FIG. 3, which is a cut-away, zoomed close-up representation of part of the needle cap body (25) and housing (4) of the device as represented in FIG. 2, one can see the relative positions of the peripheral flange (41), the proximal extremity (62) of the switch activation ridge (61), and the activation switch (53). In this figure, the proximal extremity (62) of the switch activation ridge (61) is located slightly distally of, but in fairly close proximity to, the activation switch (53). One can observe that the peripheral flange is approximately aligned with the activation switch (53), or expressed alternatively, the activation switch is positioned above the outer surface of the needle guard body (25), distally but adjacent to the needle guard body's proximal extremity (26). This representation corresponds to the initial, or zero position, in which the device is waiting to be used, and in which the device cap (80) has not yet been removed.

Figure 4:
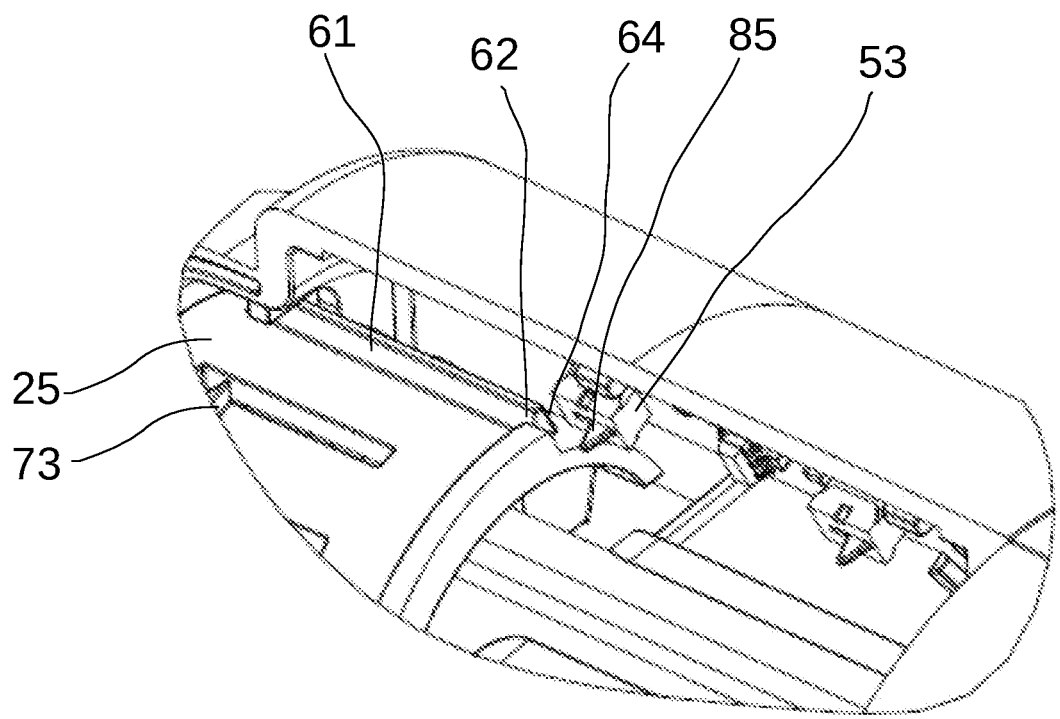
FIG. 4 is a schematic magnified torn away perspective representation showing another detail of a needle guard comprised in the single-use, disposable, drug delivery assembly of the device shown in FIG. 2.
Figure 5:
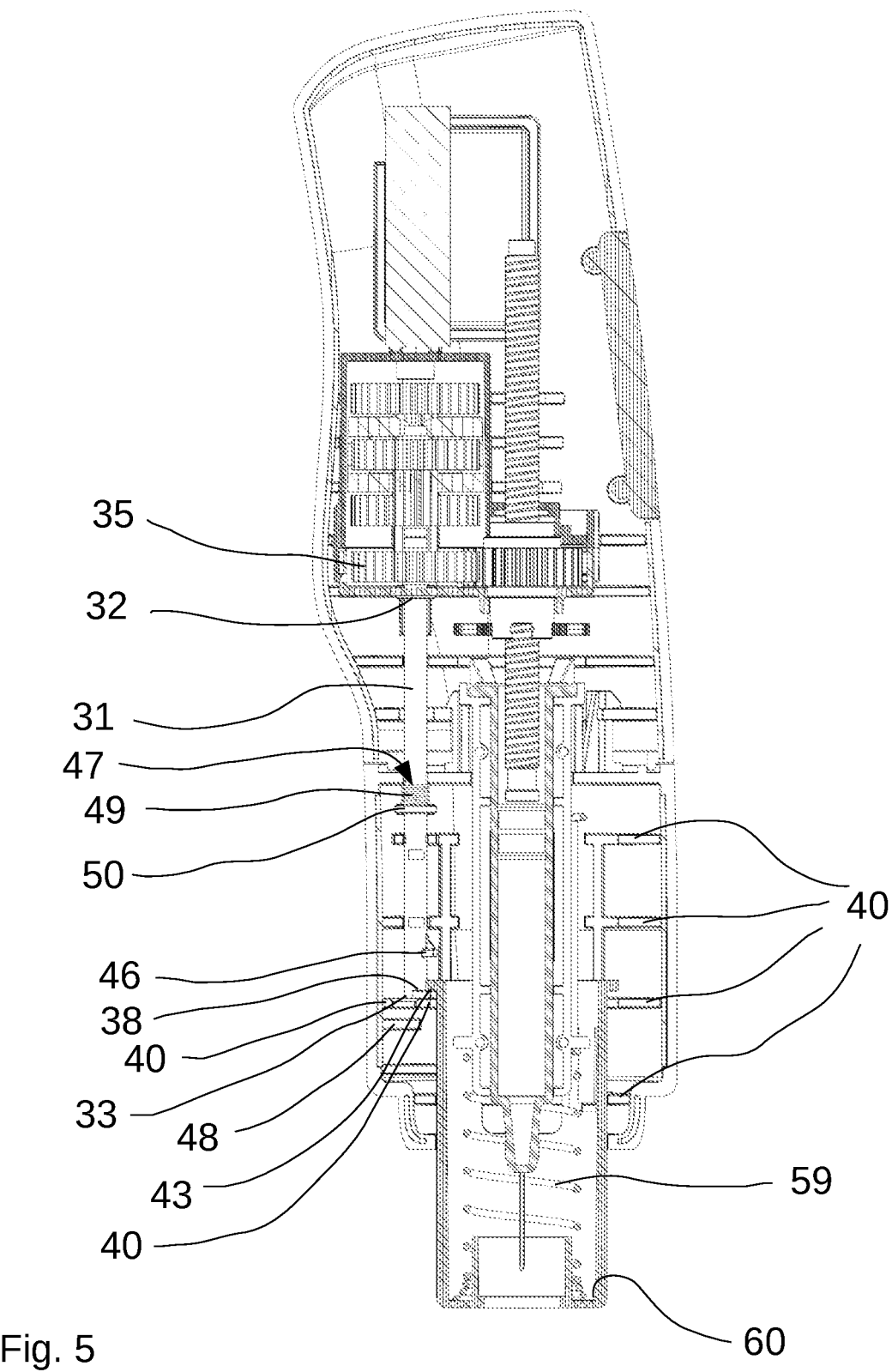
FIG. 5 is a schematic cross-sectional representation of an automatic injector device according to the invention.
Figure 6:
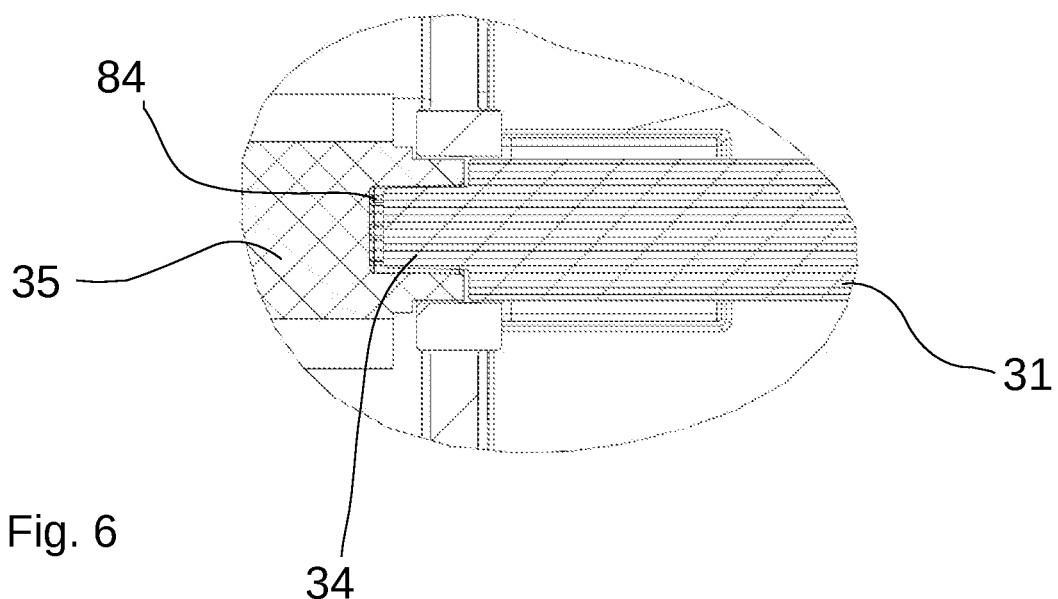
FIG. 6 is a further schematic magnified torn away perspective representation showing a detail of proximal extremity of a needle guard brake comprised in the single-use, disposable, drug delivery assembly of the device shown in FIG. 5.

Turning now for comparison to FIGS. 4, 5, and 6, these figures show the relative positioning of the components of the drug delivery assembly after the device cap (80) has been removed. When that occurs, the needle guard body (25) is moved in a distal direction by virtue of the kinetic energy stored in the coiled spring (59) pushing against the inner surface (60) of the distal extremity (27) of the needle guard body (25). The result of this movement in a distal direction is that the distal surface (42) of the peripheral flange (41) comes into abutment with the proximal surface (38) of the distal abutment (37) of the needle brake (30), and the needle body (25) is consequently blocked against further movement in a distal direction. The resulting position, as described herein, is the first, or shielding position, because the needle guard still shields the needle (11) from exposure to the user. At the same time, the corresponding relative positions of the switch engagement ridge (61) and activation switch (53) are represented in FIG. 4. As can be observed from FIG. 4, the proximal extremity (62) of the switch engagement ridge (61) has now shifted in a distal direction further away from the activation switch (53), and the latter can be seen to now be in a free space with regard to the proximal extremity (26) of the needle guard body (25). Similarly, as illustrated in FIG. 6, with a close-up representation of the proximal extremity (32) of the needle brake, one can observe that the drive motor engagement means (34) in the first, shielding position, are held by, and cooperate with, a toothed cog (84), which is mounted on, or integrated into, and axially aligned with, the drive motor gear (35).

Figure 7:
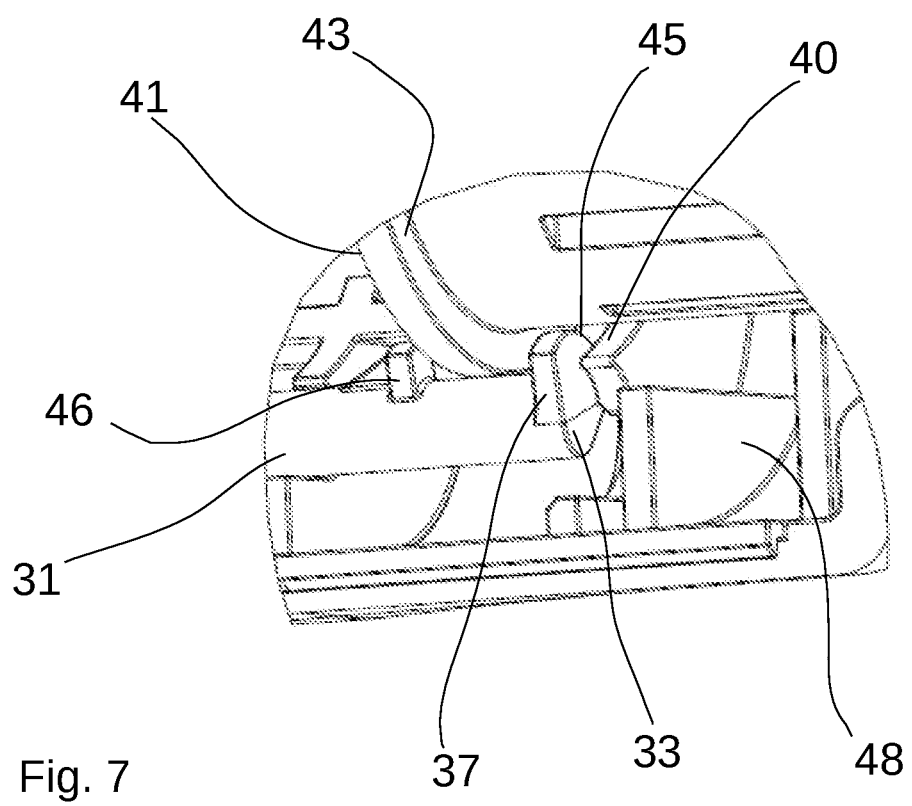
FIG. 7 is a schematic magnified torn away perspective representation showing a detail of a distal extremity of a needle guard brake comprised in the single-use, disposable, drug delivery assembly of the device shown in FIG. 5.
Figure 8:
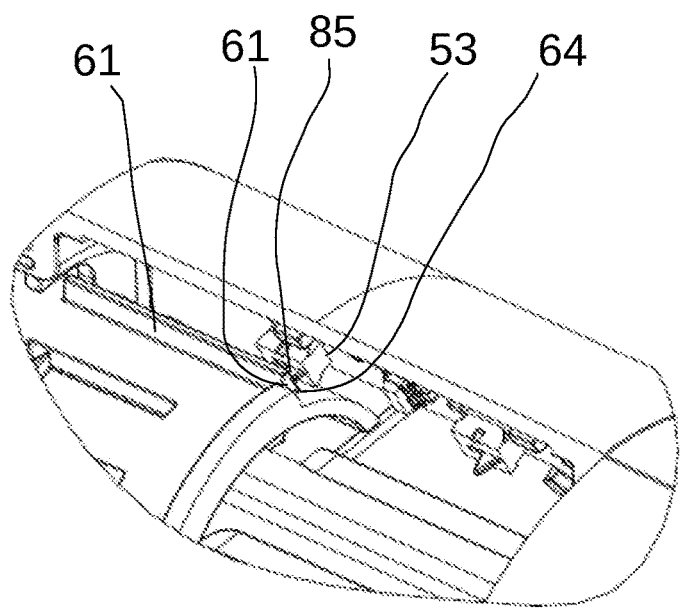
FIG. 8 is a schematic magnified torn away perspective representation showing a further detail of a needle guard comprised in the single-use, disposable, drug delivery assembly of the device according to the invention.

As illustrated in more detail by FIG. 7, when the distal extremity (27) of the needle guard body (25) is pushed onto a surface, for example, and in normal use, the skin of a user, the needle guard body slides backwards, or proximally, and coaxially along the longitudinal axis (8a) of the syringe assembly inside the housing (4). In so doing, the distal surface (42) of the peripheral flange (41) moves out of abutment with the proximal surface (38) of the distal abutment (37) of the needle brake (30). Both the peripheral flange (41) and the activation switch ridge (61) are thus moved simultaneously in a proximal direction towards the second, "injection-ready" position. The proximal extremity (62) of the activation switch ridge (61), and of course by extension, the needle guard, thereby reach the third position of the device, intermediate between the first, shielding position, described above, and the second, injection-ready position, in which said activation switch ridge (61) comes into contact, via the angled ridge surface (64), with the activation switch (53). In this third, "activation" position, the angled surface ridge (64) pushes against a spring-loaded projection (85) of the activation switch (53) and electrically closes the circuit, causing generation of a wake-up signal, for example, an electric current. The generated wake-up signal is received by the programmable control system (54), which in turn wakes up the remainder of the device and distributes power to the other circuits in the device. Waking of the device via activation of the wake-up switch (53) therefore causes the skin sensor circuit (57) to be powered up. The activation step and subsequent activation of the skin sensor circuit are quasi-instantaneous or quasi-simultaneous, with the result that virtually as soon as the activation switch ridge (61) has caused the activation switch (53) to close the activation circuit (51), then the skin sensor is already in a position to determine whether the distal extremity of the device is in sufficiently close proximity to the skin of a user. As a result, under normal use conditions, as the user brings the distal extremity (27) of the needle guard body onto, or sufficiently near the skin, the capacitive resistance surface (58) will be active. Any changes in electrical capacitance or electrical resistance caused by skin contact or near-contact at the capacitive resistance surface will be detected by the skin sensor circuit (57) via the electrical connection provided by the coiled spring (59). In the event that the skin sensor circuit (57) determines that the device is in suitable contact or proximity to the skin, then a corresponding signal will be sent to the programming control system (54). However, in the event that the skin sensor circuit doesn't detect the sufficient proximity, or contact, of skin with the distal extremity of the needle guard, then no corresponding signal will be sent to the programmable control system (54), and no corresponding signal will be sent by the programmable control system to release, or disengage, the needle brake (30). As a consequence, and as illustrated by FIGS. 7 and 8, further proximal travel of the needle guard that might have caused the needle to become unshielded, will be prevented, because the proximal surface (43) of the peripheral flange (41) will abut against the abutment projection (46) provided on the cylindrical body (31) of the needle brake (30). From the above description, it will be apparent to the reader that the activation switch (53) and activation switch ridge (61) are positioned relative to each other such that the third, intermediate, "activation" position is reached before the proximal surface (43) of the peripheral flange (41) comes into abutment with the abutment projection (46). Such relative position further ensures that disengagement of the needle brake (30) occurs before the peripheral flange (41) encounters the abutment projection (46), thereby guaranteeing smooth operation for the user, with no jolting during use of the device to carry out the injection procedure. To all intents and purposes, the abutment projection (46) is one of the safety elements of the device, in that it prevents unauthorized attempts to cause the needle to protrude outside of the needle guard (24) if no skin contact has been detected by the skin sensor circuit (57).

Figure 9:
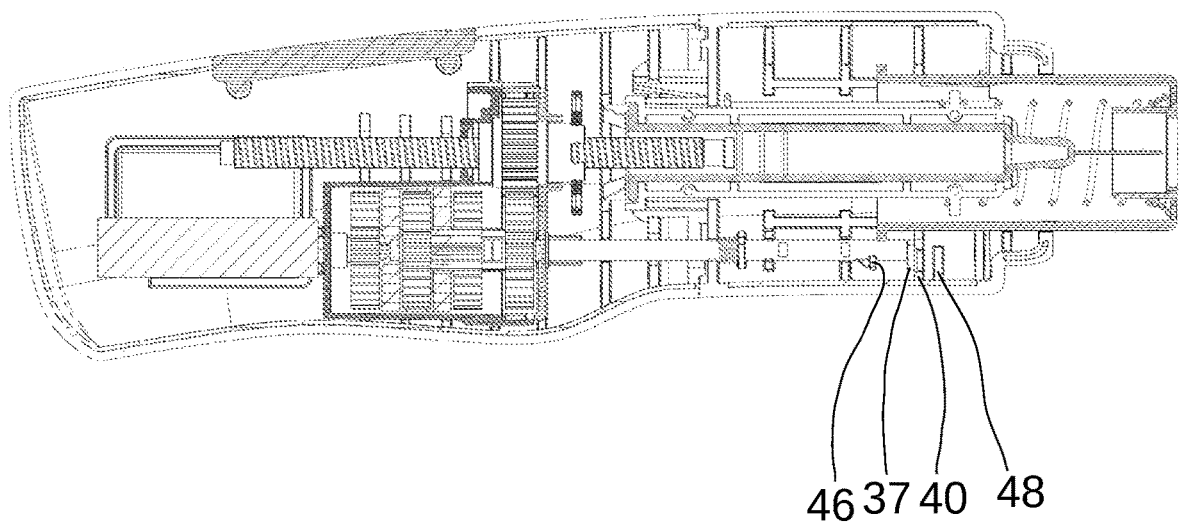
FIG. 9 is a further schematic cross-sectional representation of an automatic injector device according to the invention.

In the event that skin contact is appropriately detected, the skin sensor circuit (57) sends a signal to the programmable control system (54). The latter will then activate, and effect, needle brake (31) disengagement by commanding the drive motor (67) to engage the drive motor gear (35) via the gear assembly (66) and cause the cylindrical body (31) of the needle brake to rotate about its longitudinal axis (8b). In so doing, the distal abutment will be rotated about an angle generally comprised between 0° and up to 180°, although preferably 180°, with the result that the distal abutment surface (39) will no longer abut the first inner wall projection (40). This situation is shown in FIG. 9.

Figure 10:
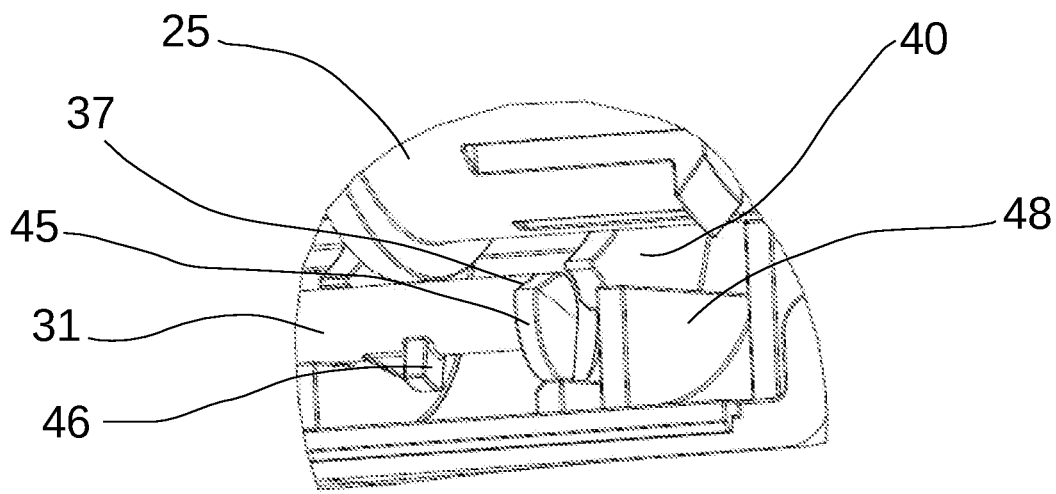
FIG. 10 is a further schematic magnified torn away perspective representation showing a detail of a distal extremity of a needle guard brake comprised in the single-use, disposable, drug delivery assembly of the device according to the invention.
Figure 11:
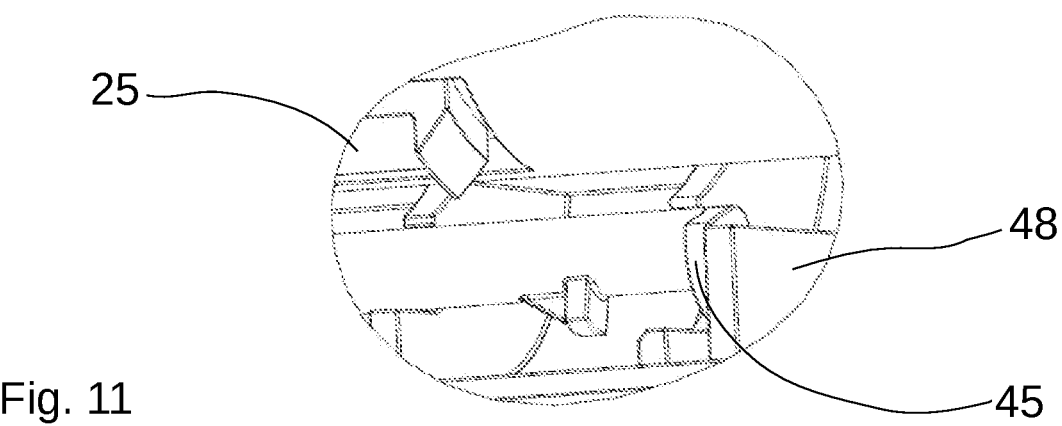
FIG. 11 is a further schematic magnified torn away perspective representation showing a detail of a distal extremity of a needle guard brake comprised in the single-use, disposable, drug delivery assembly of the device according to the invention.
Figure 12:
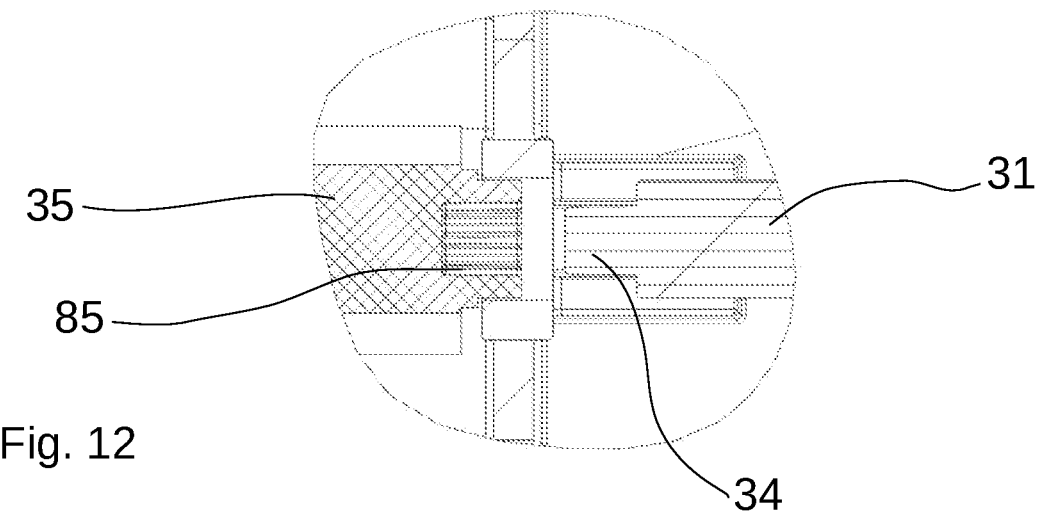
FIG. 12 is a further schematic magnified torn away perspective representation showing a detail of a proximal extremity of a needle guard brake comprised in the single-use, disposable, drug delivery assembly of the device according to the invention.

FIG. 10 shows a close-up representation of the distal abutment (37) after rotation of the cylindrical body (31). One can observe that the arcuate edge (45) has moved away from the first inner wall projection (40) and as a result the distal abutment surface (39) is no longer in abutment with said first inner wall projection (40). As shown in FIG. 10, the distal abutment has been shaped to now be able to translate, under the impetus of the released kinetic energy of the coiled spring (50) and collar (51), in a distal direction so that said distal abutment surface comes into abutting contact with said second inner wall projection (48). As a result, the needle guard body (25) can continue to move in a proximal direction towards the second, injection ready, position, as illustrated in FIG. 11. Corresponding disengagement of the needle brake at the proximal extremity (32) of the cylindrical body (31) is illustrated in FIG. 12, where one can observe that gear engagement means (34) have become disengaged from the toothed cog (84) and the drive motor gear (35).

Figure 13:
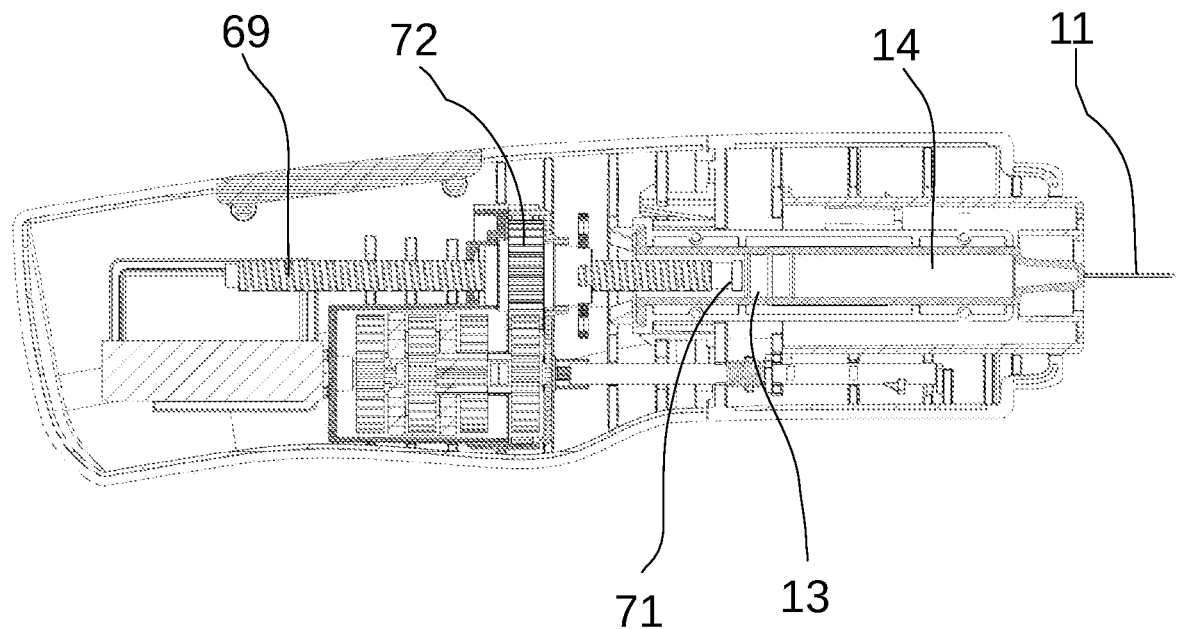
FIG. 13 is a further schematic cross-sectional representation of an automatic injector device according to the invention.

FIG. 13 illustrates an overall view according to a schematic cross-sectional representation of the device after the needle brake has been released, or disengaged from the drive motor gear, and the distal abutment surface (39) of the distal extremity (37) of the cylindrical body (31) has been pushed distally by coiled spring (50) and collar (51) into distal abutment with the second inner wall projection (48).

Figure 14:
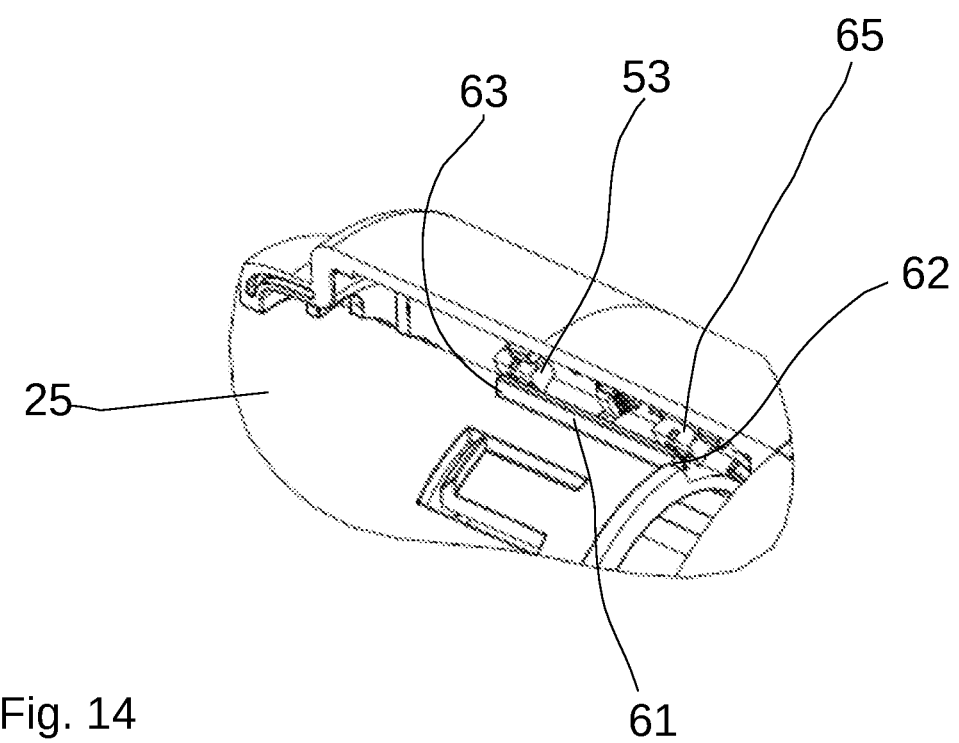
FIG. 14 is a further schematic magnified torn away perspective representation showing a detail of a distal extremity of a needle guard comprised in the single-use, disposable, drug delivery assembly of the device according to the invention.

FIG. 14 illustrates a close-up view with partial removal of the needle guard showing the relative positions of the needle guard in the second, "injection ready" position. As can be observed from FIG. 14, the needle guard body (25) has been moved back as far as it can in the proximal direction, with the effect mat the angled ridge surface (64) of the switch activation ridge (61) covers and engages the spring-loaded projections of both the activation switch (53) and the "injection-ready" switch. The device is now ready to activate the injection step. As soon as both switches are activated, or as soon as the switch activation means has reached the second, "injection ready" position, a corresponding "injection-ready" signal is sent to the programmable control system (54), which responds by commanding the drive motor (67) and gear assembly (66) to drive the piston gear (72) forward in a distal direction so that the distal extremity of the screw thread piston (69) engages with the plunger (13) of the syringe assembly (5) and pushes said plunger in a distal direction to expel the drug out of the drug containing chamber, through the needle and into the intended recipient of the drug.

Figure 15:
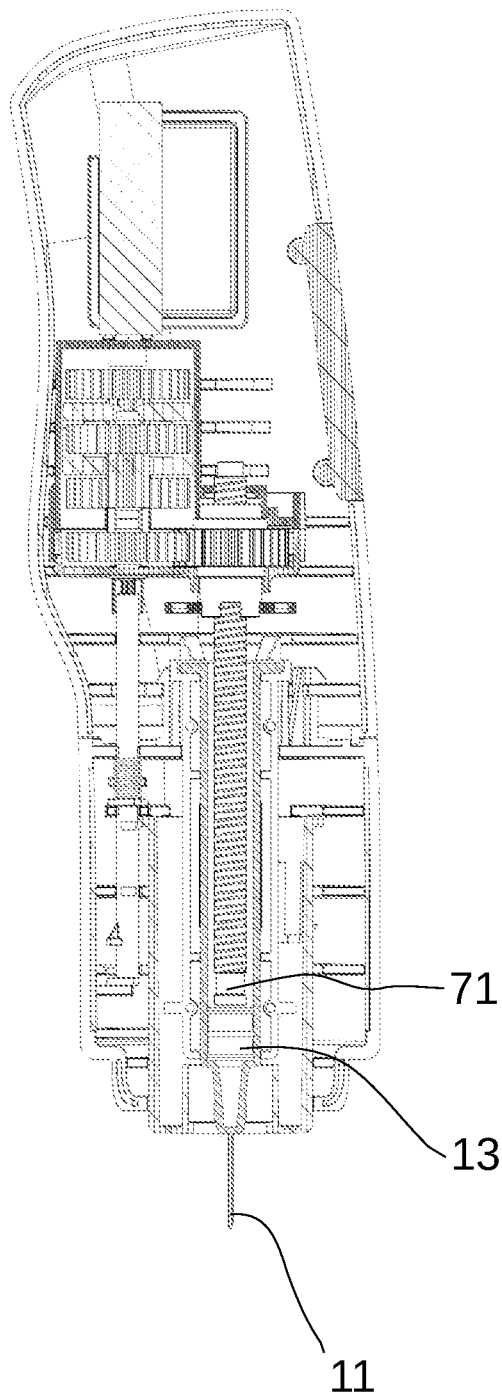
FIG. 15 is a further schematic cross-sectional representation of an automatic injector device according to the invention.

FIG. 15 illustrates the relative positions of the components of the automatic injector device once the injection step has been completed. As can be observed from FIG. 15, the piston (72) has pushed the plunger (13) in the distal direction to the distal extremity of the syringe body (6), and all corresponding drug contained within the drug chamber (14) has been expelled. The drive motor (67) will for a very short while keep attempting to drive the plunger (13) forward in a distal direction, and the increasing resistance met by the gears and drive motor in attempting to do so will result in increased electrical consumption as the motor (67) adapts its work output to try and overcome that resistance. This increase in workload can be fed back into the programmable control system (54), and a corresponding "injection end" signal created by the programmable control system, indicating that all circuits should be shut down, upon which the programmable control system acts accordingly by shutting off power to the motor, and other circuits. At the same time, an "injection end" or other similar signal can be displayed or communicated to the user, e.g. via LEDs or sound, to indicate that the distal extremity (27) of the needle guard body (25) can be moved away from the skin.

Figure 16:
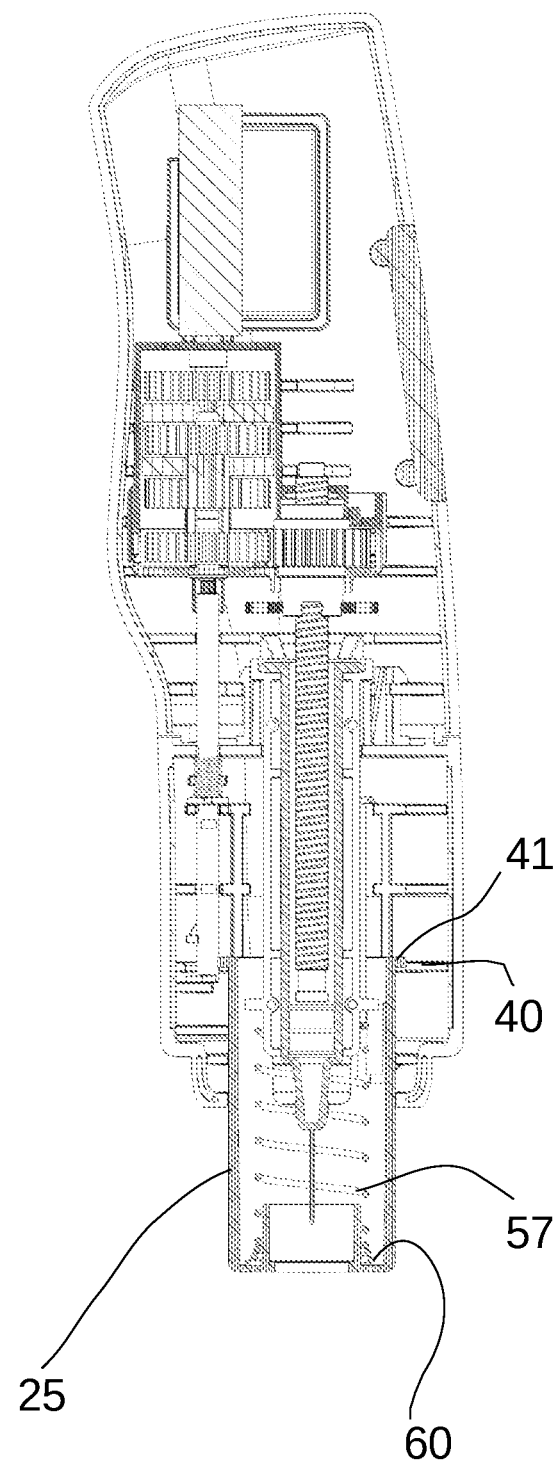
FIG. 16 is a further schematic cross-sectional representation of an automatic injector device according to the invention.
Figure 17:
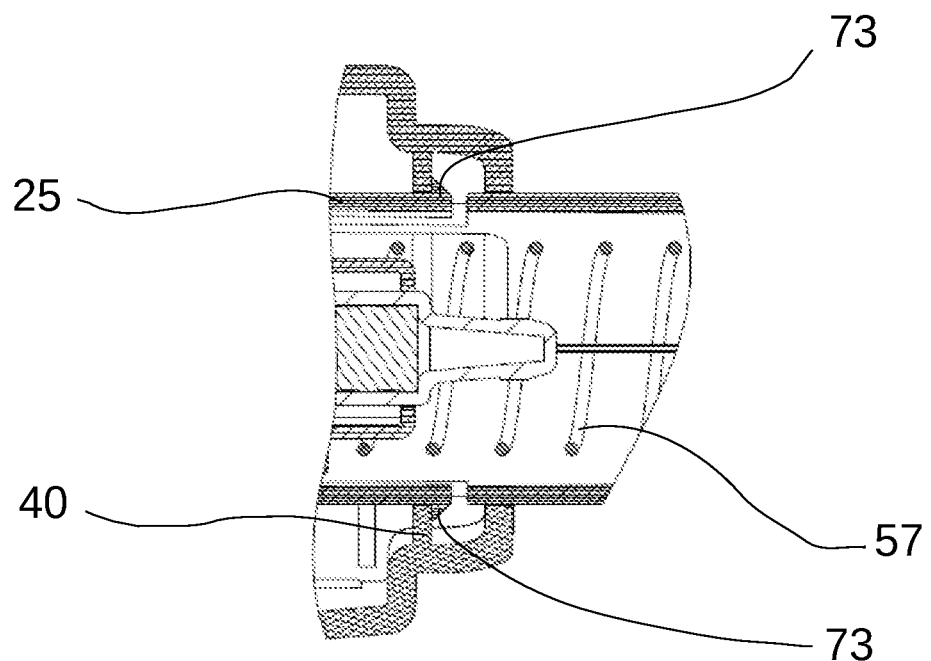
FIG. 17 is a further schematic magnified cross-sectional representation showing a detail of a distal extremity of a needle guard comprised in the single-use, disposable, drug delivery assembly of the device according to the invention.
Figure 18:
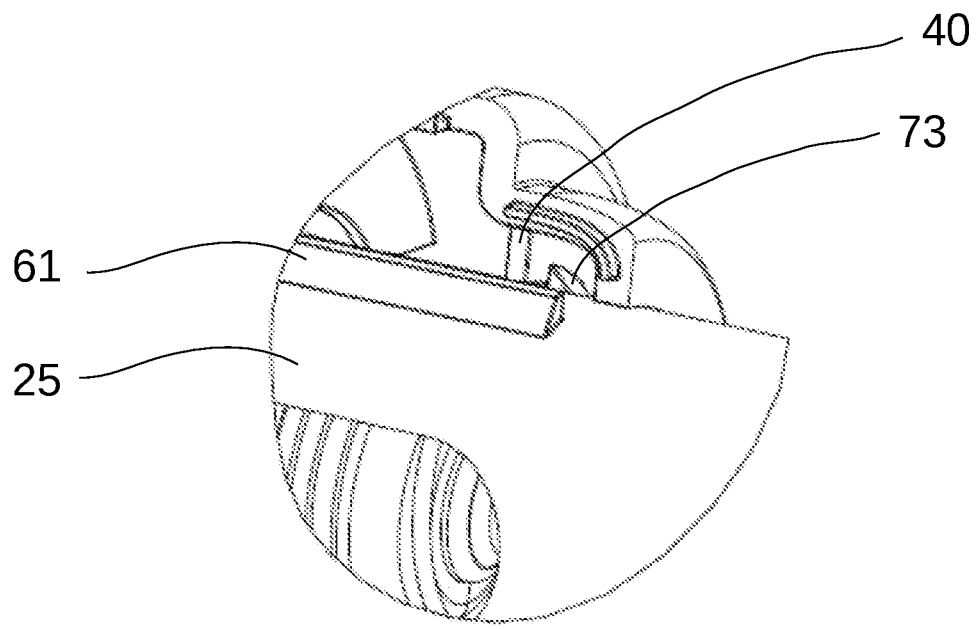
FIG. 18 is a further schematic magnified torn away perspective representation showing a detail of a distal extremity of a needle guard comprised in the single-use, disposable, drug delivery assembly of the device according to the invention.

As the user removes the needle guard body from the skin, or distances the skin from the end of the needle guard body (25), and as illustrated in FIGS. 16, 17 and 18, the needle guard body (25) now moves forward in a distal direction again under the effect of the released kinetic energy that was stored in the coiled spring (57) and which was in abutment against the inner wall (60) of the distal extremity of the needle guard body (25). As the energy stored in the coil is released, so the coiled spring moves from a constrained, to an unconstrained, or relatively unconstrained, configuration. The distal direction of movement of the needle guard body (25) is such that it causes the needle guard body (25) to shield, once again, the needle (13), totally covering it, as the body (25) moves into its final position. The final, fourth, and irreversible position is reached when the edge (44) of the peripheral flange (41) is approximately level with a reduced diameter inner wall projection (40) provided on the housing (4) in proximity to the distal extremity of the latter. The edge (44) of the peripheral flange (41) abuts against the inner wall projection to prevent any user from wiggling or attempting to laterally displace the needle guard body (25) outside of the longitudinal axis (8a). Additionally, the hooked projections (73) provided on the needle guard body expand elastically and radially after passing through the reduced diameter inner wall projection, preventing any attempt to push the needle guard body back into the housing in a proximal direction, and thereby preventing any future use of the needle or syringe assembly. The drug delivery assembly (2) can thereafter be detached from the transmission assembly (3) and disposed of in an appropriate manner whilst the drive transmission assembly can be re-used after reconnecting with a new, unused, drug delivery assembly.

The invention claimed is:

1. An automatic injector device comprising:
a single-use, disposable, drug delivery assembly comprising a housing and a syringe assembly located at least partially within the housing, said syringe assembly including a plunger, a pre-filled unit-dose drug containing chamber, and needle, said plunger, drug containing chamber and needle being configured and dimensioned to function as an injection syringe, and
a needle guard coaxially movable along the longitudinal axis between a first, shielding position completely covering a distal extremity of the needle, and a second, injection-ready position;
wherein the drug delivery assembly housing further comprises an activation circuit configured to electrically wake up the automatic injector device when the needle guard is moved into a third, wake-up position;
a reusable motorized transmission assembly comprising a housing, a programmable control system, a motor, and a transmission assembly located within the housing, said transmission assembly being configured and dimensioned to engage the plunger of said syringe in the drug delivery assembly and expel said unit dose drug from the drug containing chamber, into the needle and out of the drug delivery assembly, wherein the programmable control system is configured to control the motor and push the plunger;
wherein said single-use disposable drug delivery assembly and said reusable motorized transmission assembly are in substantial axial alignment along a longitudinal axis defined by the syringe, plunger, pre-filled unit-dose drug containing chamber, and needle; and
wherein the housing of the single-use, disposable, drug delivery assembly is removably coupled to the housing of the reusable motorized transmission assembly via a coupling system configured and dimensioned to provide substantial axial alignment between said single-use disposable drug delivery assembly and said reusable motorized transmission assembly.

2. The automatic injector device according to claim 1, wherein the coupling system is operable by hand.

3. The automatic injector device according to claim 1, wherein the coupling system enables substantially axially aligned coupling of the single-use, disposable, drug delivery assembly and the reusable motorized transmission assembly together in that said coupling system comprises snap lock coupling members comprising a male, insertion part and a corresponding female, receiving part, disposed at one of a distal extremity of the housing of said reusable motorized transmission assembly and a proximal extremity of the housing of said single-use disposable drug delivery assembly or vice-versa.

4. The automatic injector device according to claim 1, wherein the coupling system enables removal of the single-use, disposable, drug delivery assembly from the reusable motorized transmission assembly in that:
    said coupling system comprises snap lock coupling members comprising a male, insertion part and a corresponding female, receiving part, disposed at one of a distal extremity of the housing of said reusable motorized transmission assembly and a proximal extremity of the housing of said single-use disposable drug delivery assembly or vice-versa; and
    said corresponding female, receiving part comprises a twist-release enabling member providing for twist-release of said male, insertion part from said female, receiving part.

5. The automatic injector device according to claim 1, wherein the needle guard is configured and dimensioned to be housed at least partially within the housing of the single use, disposable, drug delivery assembly, and between the first, shielding position completely covering the distal extremity of the needle, and the second, injection-ready position.

6. The automatic injector device according to claim 1, wherein the needle guard is configured and dimensioned to be housed at least partially within the drug delivery assembly housing, and coaxially movable along the longitudinal axis between the first, shielding position completely covering the distal extremity of the needle, the second, injection-ready position, and the third, wake-up position.

7. The automatic injector device according to claim 1, wherein the needle guard is configured and dimensioned to be housed at least partially within the drug delivery assembly housing, and coaxially movable along the longitudinal axis between the first, shielding position completely covering the distal extremity of the needle, the second, injection-ready position, the third, wake-up position, and a fourth, irreversible, safety position located distally of said first position.

8. The automatic injector device according to claim 1, wherein the drug delivery assembly further comprises a needle guard brake, wherein: the needle guard is configured and dimensioned to be housed at least partially within the drug delivery assembly housing, and is coaxially movable along the longitudinal axis between at least the first, shielding position completely covering the distal extremity of the needle, and at least the second, injection position; and the needle guard brake is configured and dimensioned to selectively engage or disengage the needle guard to restrict and/or allow coaxial movement of said needle guard between the at least first, shielding position completely covering the distal extremity of the needle, and the second, injection position.

9. The automatic injector device according to claim 1, the drug delivery assembly further comprises a needle guard brake, wherein said needle guard brake comprises:
    a longitudinal body, housed at least partially within the drug delivery assembly housing and having an own longitudinal axis disposed in spaced apart parallel alignment with the longitudinal axis of the syringe assembly, the longitudinal body having a proximal extremity and a distal extremity.

10. The automatic injector device according to claim 9, wherein said needle guard brake further comprises drive motor gear engagement means located at the proximal extremity of the longitudinal body, configured and dimensioned to engage with, and be releasable from, a drive motor gear housed within the reusable motorized transmission assembly.

11. The automatic injector device according to claim 10, wherein said drive motor gear engagement means located at the proximal extremity of the longitudinal body comprises a grooved bore located proximate, and extending up to, the proximal extremity of said longitudinal body.

12. The automatic injector device according to claim 9, wherein said needle guard brake further comprises an abutment located at the distal extremity of the longitudinal body, said distal extremity abutment comprising a distal abutment surface and a proximal abutment surface, the distal abutment surface of the abutment located at the distal extremity being configured and dimensioned to engage: before use of the device, in the first, shielding position, with a first inner wall surface of the drug delivery assembly housing.

13. The automatic injector device according to claim 9, wherein said needle guard brake further comprises an abutment located at the distal extremity of the longitudinal body, said distal extremity abutment comprising a distal abutment surface and a proximal abutment surface, the proximal abutment surface of the distal abutment being configured and dimensioned to engage: before use of the device, in the first, shielding position, with a distal surface of a peripheral flange of the needle guard.

14. The automatic injector device according to claim 13, wherein said needle guard brake further comprises an intermediate abutment projection located on a peripheral surface of the longitudinal body between said distal and proximal extremities, which abutment projection engages with a proximal surface of the peripheral flange of the needle guard after said needle guard has moved past the third, wake-up position.

15. The automatic injector device according to claim 9, wherein the needle guard brake is further defined in that distal extremity abutment surfaces and an intermediate abutment projection are in substantial alignment on the longitudinal body.

16. The automatic injector device according to claim 9, wherein the motor housed within said reusable motorized transmission assembly housing comprises a toothed drive motor gear configured and dimensioned to engage with corresponding grooves of a drive motor gear engagement means located at the proximal extremity of the longitudinal body.

17. The automatic injector device according to claim 9, wherein said needle guard brake further comprises a pre-constrained elastic disengagement assembly configured and dimensioned to:
    disengage a drive motor gear engagement means of the longitudinal body from a drive motor gear; and
    bias said longitudinal body in a distal direction towards a second inner wall surface of the drug delivery assembly housing, where the second inner wall surface is different to and located in a distal direction from a first inner wall surface.

18. The automatic injector device according to claim 17, wherein a pre-constrained elastic disengagement assembly comprises:
   a coiled spring; and
   a retaining collar,
   the coiled spring being mounted around the longitudinal body and in biasing abutment against the retaining collar;
   the retaining collar being formed around said longitudinal body and projecting radially therefrom;
   the pre-constrained elastic disengagement assembly being located on the longitudinal body at a fixed position between the proximal extremity and an abutment projection of the longitudinal body.

19. The automatic injector device according to claim 9, wherein a distal extremity abutment surface of a longitudinal abutment on the longitudinal body is configured and dimensioned to engage:
   after disengagement of the needle brake, with the second inner wall surface of the drug delivery assembly housing, a second inner wall surface being different to, and located in a distal direction from a first inner wall surface.

20. The automatic injector device according to claim 1, wherein the activation circuit comprises a wake-up microswitch configured to send an activation or wake-up signal to the programmable control system, said activation signal being generated when the needle guard is moved into the third, or wake-up position over said switch.

21. The automatic injector device according to claim 1, wherein the drug delivery assembly housing further comprises a skin sensor circuit is configured to determine whether a distal extremity of the needle guard is in contact with, or in close proximity to, the skin of a user.

22. The automatic injector device according to claim 1, wherein the skin sensor circuit is connected to a capacitive resistance surface area located at the distal extremity of the needle guard.

23. The automatic injector device according to claim 1, wherein the capacitive resistance surface area and the skin sensor circuit are connected electrically via a coiled spring located within the needle guard and coaxially mounted around the syringe assembly.

24. The automatic injector device according to claim 1, wherein the activation circuit is connected to the programmable control system located within the reusable motorized transmission assembly via a severable electrical connection.

25. The automatic injector device according to claim 1, wherein the needle guard further comprises switch activation means.

26. The automatic injector device according to claim 25, wherein said switch activation means is a switch engagement ridge located longitudinally in axial longitudinal alignment with the longitudinal axis along an outer surface of said needle guard.

27. The automatic injector device according to claim 25, wherein said switch activation means is a contiguous switch engagement ridge located along an outer surface of said needle guard.

28. The automatic injector device according to claim 25, wherein said switch activation means is formed by a plurality of non-contiguous switch engagement ridges located in axial alignment along an outer surface of said needle guard.

29. The automatic injector device according to claim 1, wherein said drug delivery assembly housing further comprises a switch activation means configured to send an injection ready signal to the programmable control system located within the reusable motorized transmission assembly, said injection ready signal being generated when the needle guard is moved into the second, injection-ready position over a switch, in which position the needle is fully exposed.

30. The automatic injector device according to claim 29, wherein the second injection ready microswitch is in longitudinal axial alignment with a first activation microswitch.

31. The automatic injector device according to claim 29, wherein the injection ready microswitch is activated by switch activation means.

32. The automatic injector device according to claim 1, wherein said transmission assembly further comprises:
   a drive motor gear assembly;
   a programmable control system configured to command and control the functioning of the automatic injector; and
   a screw threaded piston having a proximal extremity and a distal extremity,
   the screw threaded piston being connected to, and driven by, a drive motor assembly via a piston drive gear of the drive motor gear assembly;
   a needle brake drive motor gear and the piston drive gear being disposed within the drive motor gear assembly in a substantially parallel and spaced apart alignment, wherein the screw threaded piston drive gear is axially aligned with a longitudinal axis of the syringe assembly, and the needle brake drive motor gear is axially aligned with the longitudinal body;
   the screw threaded piston engaging the plunger of the syringe via the distal extremity of said screw threaded piston in response to programmed motor driven movement of the drive motor gear assembly;
   said programmed motor driven movement being commanded and controlled by the programmable control system.

33. The automatic injector device according to claim 32, wherein the programmable control system is configured to determine completion of an injection cycle by electrical power consumption analysis of a drive motor.

34. The automatic injector device according to claim 1, wherein the programmable control system is configured to effect any one of the operations comprising: receiving a wake-up signal from a wake-up switch to wake the device and provide electrical power to the device; receiving a signal from a skin sensor indicating that the needle guard is in proximity to, or in contact with, the skin of a user; in response to receiving such a skin sensor signal, commanding and controlling a drive motor and a drive motor gear assembly to cause a drive motor gear to rotate the longitudinal body about its longitudinal axis and thereby cause a distal abutment and an abutment projection to move out of abutment alignment, thereby disengaging a needle brake and allowing free proximal movement of the needle guard to the second, injection ready position; upon receipt of a signal from the activation circuit that the needle guard has reached the second, injection position, command and control the drive motor and drive motor gear assembly to cause a screw threaded piston drive gear to rotate and drive a screw thread towards the plunger; continue to drive the screw thread distally onto the plunger until it is determined that an injection cycle is completed.

35. An automatic injector device comprising:
   a single-use, disposable, drug delivery assembly comprising a housing and a syringe assembly located at least partially within the housing, said syringe assembly including a plunger, a pre-filled unit-dose drug containing chamber, and needle, said plunger, drug containing chamber and needle being configured and dimensioned to function as an injection syringe;

a reusable motorized transmission assembly comprising a housing, a motor and transmission assembly located within the housing, said transmission assembly being configured and dimensioned to engage the plunger of said syringe in the drug delivery assembly and expel said unit dose drug from the drug containing chamber, into the needle and out of the drug delivery assembly;

wherein said single-use disposable drug delivery assembly and said reusable motorized transmission assembly are in substantial axial alignment along a longitudinal axis defined by the syringe, plunger, pre-filled unit-dose drug containing chamber, and needle;

wherein the housing of the single-use, disposable, drug delivery assembly is removably coupled to the housing of the reusable motorized transmission assembly via a coupling system configured and dimensioned to provide substantial axial alignment between said single-use disposable drug delivery assembly and said reusable motorized transmission assembly; and a needle guard coaxially movable along the longitudinal axis between a first, shielding position completely covering a distal extremity of the needle, and a second, injection-ready position; and wherein the drug delivery assembly housing further comprises an activation circuit configured to electrically wake up the automatic injector device when the needle guard is moved into a third, wake-up position.

36. An automatic injector device comprising:

a single-use, disposable, drug delivery assembly comprising a housing and a syringe assembly located at least partially within the housing, said syringe assembly including a plunger, a pre-filled unit-dose drug containing chamber, and needle, said plunger, drug containing chamber and needle being configured and dimensioned to function as an injection syringe;

a reusable motorized transmission assembly comprising a housing, a motor and transmission assembly located within the housing, said transmission assembly being configured and dimensioned to engage the plunger of said syringe in the drug delivery assembly and expel said unit dose drug from the drug containing chamber, into the needle and out of the drug delivery assembly;

wherein said single-use disposable drug delivery assembly and said reusable motorized transmission assembly are in substantial axial alignment along a longitudinal axis defined by the syringe, plunger, pre-filled unit-dose drug containing chamber, and needle;

wherein the housing of the single-use, disposable, drug delivery assembly is removably coupled to the housing of the reusable motorized transmission assembly via a coupling system configured and dimensioned to provide substantial axial alignment between said single-use disposable drug delivery assembly and said reusable motorized transmission assembly; and wherein said single-use, disposable, drug delivery assembly further comprises a needle guard comprising switch activation means, wherein said switch activation means is a switch engagement ridge located longitudinally in axial longitudinal alignment with the longitudinal axis along an outer surface of said needle guard.

* * * * *